US011628237B2

United States Patent
Harrell

(10) Patent No.: US 11,628,237 B2
(45) Date of Patent: Apr. 18, 2023

(54) COLLAGEN COMPOSITIONS AND USES FOR BIOMATERIAL IMPLANTS

(71) Applicant: MAM Holdings of West Florida, L.L.C., Tarpon Springs, FL (US)

(72) Inventor: Carl Randall Harrell, Tarpon Springs, FL (US)

(73) Assignee: MAM Holdings of West Florida, L.L.C., Palm Harbor, FL (US)

( * ) Notice: Subject to any disclaimer, the term of this patent is extended or adjusted under 35 U.S.C. 154(b) by 0 days.

(21) Appl. No.: 16/033,803

(22) Filed: Jul. 12, 2018

(65) Prior Publication Data

US 2019/0015548 A1  Jan. 17, 2019

Related U.S. Application Data

(63) Continuation of application No. 15/069,537, filed on Mar. 14, 2016, now abandoned, which is a continuation-in-part of application No. 13/798,742, filed on Mar. 13, 2013.

(60) Provisional application No. 62/132,571, filed on Mar. 13, 2015, provisional application No. 62/132,559, filed on Mar. 13, 2015, provisional application No. 61/610,570, filed on Mar. 14, 2012.

(51) Int. Cl.

| A61L 27/24 | (2006.01) |
|---|---|
| A61K 38/39 | (2006.01) |
| A61K 35/50 | (2015.01) |
| A61K 45/06 | (2006.01) |
| A61L 27/54 | (2006.01) |
| A61L 27/36 | (2006.01) |
| A61L 27/38 | (2006.01) |
| A61L 27/60 | (2006.01) |

(52) U.S. Cl.
CPC .............. *A61L 27/24* (2013.01); *A61K 35/50* (2013.01); *A61K 38/39* (2013.01); *A61K 45/06* (2013.01); *A61L 27/362* (2013.01); *A61L 27/3604* (2013.01); *A61L 27/3687* (2013.01); *A61L 27/3804* (2013.01); *A61L 27/54* (2013.01); *A61L 27/60* (2013.01); *A61L 2400/06* (2013.01); *A61L 2430/18* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| 5,002,071 A | 3/1991 | Harrell |
| 5,501,661 A | 3/1996 | Cartmell |
| 5,800,372 A | 9/1998 | Bell |
| 6,710,100 B1 | 3/2004 | Lipman |
| 8,283,414 B2 | 10/2012 | Yu |
| 2002/0090725 A1* | 7/2002 | Simpson ............... D01F 1/10 435/402 |
| 2003/0032143 A1* | 2/2003 | Neff ................. A61L 24/102 435/69.1 |
| 2004/0048796 A1 | 3/2004 | Hariri |
| 2007/0020225 A1 | 1/2007 | Abramson |
| 2007/0021704 A1 | 1/2007 | Hariri |
| 2008/0181935 A1 | 7/2008 | Bhatia |
| 2009/0054350 A1 | 2/2009 | Tayot |
| 2009/0202616 A1 | 8/2009 | Chong |
| 2010/0318048 A1 | 12/2010 | Hoefinghoff |
| 2011/0130710 A1 | 6/2011 | Becker |
| 2011/0218472 A1 | 9/2011 | Mirzadeh |
| 2011/0257666 A1 | 10/2011 | Ladet |
| 2011/0269667 A1 | 11/2011 | Shoseyov |
| 2012/0189586 A1* | 7/2012 | Harrell ................. A61P 43/00 424/93.7 |
| 2012/0189588 A1 | 7/2012 | Nahas |
| 2013/0245528 A1* | 9/2013 | Harrell ................. A61L 27/54 602/50 |
| 2016/0186131 A1 | 6/2016 | Voytik-Harbin |

FOREIGN PATENT DOCUMENTS

WO     9003155     4/1990

OTHER PUBLICATIONS

Boos et al. ("Collagen Types I, III and IV in the Placentome and Interplacentomal Maternal and Fetal Tissues in Normal Cows and in Cattle with Retention of Fetal Membranes," Cells Tissues Organs 2003; 174: 170-183) (Year: 2003).*
Stone et al. (Physiology, Growth Factor. [Updated May 13, 2020], In: StatPearls [Internet], Treasure Island (FL): StatPearls Publishing; Jan. 2020-. Available from: www.ncbi.nlm.nih.gov/books/NBK442024/) (Year: 2020).*
International Society for Stem Cell Research ("Stem Cell Facts" 2020 Available from: www.closerlookatstemcells.org/wp-content/uploads/2018/10/stem-cell-facts.pdf) (Year: 2020).*
Collagen Solutions (2020, Available from: www.collagensolutions.com) (Year: 2020).*
SimpurityTM Collagen Powder product information at Wound Source (2020, Available from: www.woundsource.com/product/simpurity-collagen-powder) (Year: 2020).*

(Continued)

*Primary Examiner* — Christina Bradley
(74) *Attorney, Agent, or Firm* — Fresh IP, PLC; Michael Anderson

(57) ABSTRACT

Compositions containing purified collagen biomaterial derived from tissues, for example, insoluble amnion, soluble amnion, soluble chorion of the human placenta, are provided. The collagen compositions can be used to promote wound healing, promote tissue regeneration, prevent or reduce scarring, reduce local inflammation, minimize tissue rejection, promote graft integration. Methods for using the collagen composition as a biomaterial implant for dermal filling, skin grafting, and hair transplantation are also provided.

18 Claims, No Drawings

(56) References Cited

OTHER PUBLICATIONS

Peppas et al. ("9.20Z—Hydrogels," Polymer Science: A Comprehensive Reference, vol. 9, 2012, pp. 385-395; see abstract) (Year: 2012).*

Adams and Ramsey, Grafts in dermatologic surgery: review and update on full- and split-thickness skin grafts, free cartilage grafts, and composite grafts, Dermatol Surg., 8pt2:1055-67 (2005).

Andrew, et al. Dialysis and concentration of p[rotein solutions, Curr Pro Immunology, A.3H.1-A.3H.5 (1997).

Bentkover, et al., The biology of facial fillers, Facial Plast Surg., 25(2):73-85 (2009).

Chamberlain, et al., Concise review: mesenchymal stem cells: their phenotype, differentiation capacity, immunological features, and potential for homing, Stem Cells, 25:2739 49 (2007).

Dazzi and Horwood, Potential of mesenchymal stem cell therapy, Curr Opin Oncol., 19:650-5 (2007).

De, et al., Regulation of trypsin activity by peptide fraction of an aqueous extract of human placenta used as wound healer, J Cell Physiol, 226:2033-40 (2011).

Fernandez-Cossio, et al., Biocompatibility of two novel dermal fillers: Histological evaluation of implants of a hyaluronic acid filler and a polyacrylamide filler, Plast Reconstr Surg., 117(6):1789-96 (2006).

Halim, et al., Biologic and synthetic skin substitutes: An overview, Indian J Plast Surg. 43(Suppl):S23 8 (2010).

Hong, et al., The effect of human placenta extract in a wound healing model, Ann Plast Surg., 65:96-100 (2010).

Hopkinson, et al., Optimization of amniotic membrane (AM) denuding for tissue engineering, Tissue Eng Part C Methods, 14:371-81 (2008).

Jacovella, Use of calcium hydroxylapatite (Radiesse) for facial augmentation, Clin Interv Aging. 3(1):161-74(2008).

Liu, et al., the use of type I and type III injectable human collagen for dermal fill: 10 years of clinical experience in China, Semin Plast Surg., 19(3): 241-50 (2005).

Loganathan, et al., Complications of hair restoration surgery: a retrospective analysis, Int J Trichology. 6(4): 168-172 (2014).

McPhie, Dailysis, Enzyme Purification and Related Techniques, 104(pt 3):23-32, Academic press, by Williiam Jakoby (1971).

Parenteau-Bareil, et al., Collagen-based biomaterials for tissue engineering applications, Materials, 3(3):1863-87 (2010).

Parsley and Perez-Meza,, Review of factors affecting the growth and survival of follicular grafts, J Cutan Aesthet Surg. 3(2): 69-75 (2010).

Phinney and Prockop, et al., Concise review: mesenchymal stem/multipotent stromal cells: the state of transdifferentiation and modes of tissue repair-current views, Stem Cells, 25:2896-2902 (2007).

Seifert, et al., Skin shedding and tissue regeneration in African spiny mice (acomys). Nature, 489(7417):561-5 (2012).

Steward, et al., Management of visible granulomas following periorbital injection of poly-L-lactic Acid, Ophthal Plast Reconstr Surg. 23(4):298-301 (2007).

Choi, et al., "Full thickness skin wound healing using human placenta-derived extracellular matrix containing bioactive molecules", *Tissue Engineering: Part A*, 19(3-4): 329-339 (2013).

\* cited by examiner

COLLAGEN COMPOSITIONS AND USES FOR BIOMATERIAL IMPLANTS

CROSS-REFERENCE TO RELATED APPLICATIONS

This application is a continuation of prior application U.S. Ser. No. 15/069,537 filed Mar. 14, 2016, entitled "COLLAGEN COMPOSITIONS AND USES FOR BIOMATERIAL IMPLANTS", by Carl Randall Harrell, which is a continuation-in-part of U.S. application Ser. No. 13/798,742, filed Mar. 13, 2013, which claims benefit of U.S. Provisional Application No. 61/610,570, filed Mar. 14, 2012. This application also claims benefit of U.S. Provisional Application No. 62/132,571, filed Mar. 13, 2015, and U.S. Provisional Application No. 62/132,559, filed Mar. 13, 2015, which are incorporated by reference in their entirety.

FIELD OF THE INVENTION

The invention relates generally to collagen compositions and methods of use in tissue regeneration and tissue augmentation, particularly in areas of dermal filling, skin grafting and hair transplantation.

BACKGROUND OF THE INVENTION

All materials intended for application in humans as biomaterials undergo tissue responses when implanted into living tissue. These responses involve wound healing responses, inflammatory, foreign body reactions, and fibrous encapsulation of the biomaterial.

One area of great interest in the use of biomaterial is dermal filling. A dermal filler is a soft tissue filler injected into the skin to help fill in facial wrinkles, restoring a smoother appearance. Unfortunately, many synthetic, non-degradable dermal fillers such as calcium hydroxyapatite (e.g. RADIESSE®, Merz Pharmaceuticals GmbH) and Poly-L-Lactic Acid (PLLA, e.g SCULPTRA®, Valeant, West Laval, QC, Canada), have been shown to form granulomas (Jacovella, P F, *Clin Intern Aging*. 3(1): 161-174 (2008); Steward D B, et al., *Ophthal Plast Reconstr Surg*. 23(4):298-301 (2007)).

Collagen, a matrix protein, has been used widely in the biomaterials area, appearing in or as various matrices, membranes, sponges, scaffolds, stents, and other devices, implanted or applied. Applications of collagen-based biomaterials range from experimental uses, osteochondral defects, vascular diseases, urogenital system, neural migration, to many skin-related applications (Parenteau-Bareil R, et al., *Materials*, 3(3), 1863-1887 (2010)).

Some FDA-approved dermal fillers commonly used in facial rejuvenation or reconstructive surgery include Bovine ZYDERM®, porcine EVOLENCE™. However, bovine and porcine collagen is significantly immunogenic in human (Bentkover S H, et al., *Facial Plast Surg*. 25(2): 073-085 (2009)).

Another area of interest is in skin grafts. Skin grafting is useful for treatment of wounds that heal very slowly or fail to heal. Skin is placed onto the wound, where typically skin cells from the graft can then migrate laterally throughout the wound surface in order to form a layer of skin. Depending on the source of skin, grafting may be in the form of an autograft, a xenograft, or an allograft. In an autograft, a patient that is sufficiently healthy for additional surgery undergoes a procedure when skin is obtained from another area of the patient's body. In a xenograft, skin is obtained from another animal, such as a pig. In an allograft, skin is obtained from another person or from donor skin from a frozen cadaver. Allografts and xenografts are a temporary measure since the patient's immune system rejects these within about ten days. After an allograft or xenograft is used and rejected, an autograft may subsequently be used (Halim, A S et al., *Indian J Plast Surg*. 43(Suppl): S23-S28 (2010)).

Skin grafting may be unsuccessful for numerous reasons. The most common reason for skin graft failure is hematoma beneath the graft. Similarly, seroma formation may prevent graft adherence to the underlying wound bed, preventing the graft from receiving the necessary nourishment. Movement of the graft or shear forces may also lead to graft failure through disruption of the fragile attachment of the graft to the wound bed. This often occurs when the graft is placed over a flexor or extensor surface or over a mobile tendon sheath (Adams D C et al., *Dermatologic Surgery*, 31.s2: 1055-1067 (2005)).

Another common source of failure is a poor recipient site. The wound may have poor vascularity, or the surface contamination may have been too great to allow graft survival. Bacteria and the inflammatory response to bacteria stimulate release of enzymes and other harmful substances at the wound interface that disrupt the fibrin adherence of the graft.

Another area of interest is in hair grafts. Hair transplantation is a surgical technique that involves moving hair follicles from a donor area to a recipient area. It is used to treat baldness and to restore eyelashes, eyebrows, and beard hair, and to fill in scars caused by accidents, disease and surgery.

Some of the challenges of hair transplantation include the loss of some implanted grafts and limited hair growth (Parsley, W M et al., *J Cutan Aesthet Surg*. 3(2): 69-75 (2010); Loganathan E L, et al., *Int J Trichology*. 6(4): 168-172 (2014)). It has been noted that at least one principal obstacle to good hair growth is the lack of vascularity. The innermost area of the graft needs to receive vascular nourishment soon after being implanted in the recipient site. If the graft does not receive adequate nutrition, it will greatly reduce the survival of the implanted hairs. For example, a mismatch of size between the graft and recipient site is thought to play a negative role in hair survival. If the graft fits too tightly, it may be compressed, which can inhibit perfusion of the graft tissue. If the graft fits too loosely, any space or loss of contact between the graft and the surrounding tissue may prevent the perfusion of vital nutrition. In addition, dehydration of the graft, which may occur in times as short as 5 minutes, can have a detrimental effect on graft survival. Other challenges associated with hair transplantation include the appearance of scars in the donor hair graft region.

There remains a need for dermal filler, with minimal immunogenicity, and good tissue repair capability.

There is a need for a skin graft that has improved structural characteristics, improved survival rates and an improved wound healing time.

There remains a need for increasing the effectiveness of hair transplantation, in particular, increasing the survival rate of implanted hair and reducing the appearance of scars and trauma to the graft donor region.

Therefore, it is an objective of the current invention to provide compositions for use as implant biomaterials with minimal immunogenicity, superior biocompatibility and biodegradability.

It is also an objective of the current invention to provide compositions that promote wound healing, stimulate tissue regeneration including growth of adipocytes and fibroblasts, and reduce or prevent scarring for therapeutic and/or aesthetic applications.

It is a further objective of the current invention to provide compositions for use for skin grafts or for hair transplantation.

SUMMARY OF THE INVENTION

It has been established that collagen, or collagen-containing compositions, promote tissue regeneration, reduce scar formation, and promote graft integration. Compositions and methods of use for collagen-containing biomaterials include Type I collagen and Type III collagen in an amount effective to promote wound healing at a site of surgery, injury, or wound relative to an untreated control. Methods of using the collagen compositions for tissue repair, or tissue augmentation in dermal filling, skin grafting, and hair grafting are also provided.

Typically, collagen compositions contain at least 30% Type III collagen by weight of the total collagen present in the composition. In a preferred embodiment, collagen compositions contain about 50% to 100% Type III collagen. The collagen composition can be extracted from any part of insoluble amnion, soluble amnion, and/or soluble chorion of human placentae. Furthermore, collagen compositions can also contain collagen-containing biomaterial such as de-cellularized human placenta extracellular matrix. Modifications to collagen compositions include sterilization, cross-linking, or removal of inter-molecular disulfide bridges to meet the desired properties of the composition for the intended purposes. In some embodiments, the removal of inter-molecular disulfide bridges is done with an alkaline solution such as 1M NaOH.

In some embodiments, de-cellularized collagen biomaterial includes one or more compounds such as antimicrobial agents, analgesic agents, local anesthetic agents, anti-inflammatory agents, immunosuppressant agents, anti-allergenic agents, enzyme cofactors, essential nutrients, growth factors, and combinations thereof. The collagen biomaterial also provides a system to deliver directly to target tissues one or more cells such as stem cells, mesenchymal stem cells, keratinocytes, fibroblasts, melanocytes, adipocytes, T lymphocytes, B lymphocytes, natural killer cells, dendritic cells, and combinations thereof.

Skin grafts and hair grafts including the collagen compositions are also described. In some embodiments the composition of collagen biomaterial is coated onto or injected into the skin graft or hair graft or at site of surgery, injury, or wound, prior to, in conjunction with, or subsequent to, implantation with the skin graft or hair graft. In a specific example, the skin graft or the hair graft is harvested from a donor site of the same subject under treatment. In a further example, the skin graft is a full-thickness graft or a split thickness graft. In yet another example, the hair graft contains one or more hair follicles. Exemplary donor site for hair grafts are the temporal or the occipital region of scalp. Exemplary recipient site for hair grafts are scalp, the facial region, armpit or chest region or the pubic region.

Methods for reducing or preventing the formation of scar tissue, promoting healing, promoting tissue regeneration, minimizing local inflammation, minimizing tissue rejection, or enhancing graft integration, including administering to a subject these collagen compositions. In some embodiments, methods for reducing or preventing the formation of scar tissue, promoting healing, promoting tissue regeneration, minimizing local inflammation, minimizing tissue rejection, or enhancing graft integration, include injecting, or topically applying the collagen composition at a site of surgery, injury, or wound. In some embodiments the subject has undergone, is undergoing, or will undergo one or more cosmetic applications to fill wrinkles, lines, folds, scars, and to enhance dermal tissue. In other embodiments, the subject has a site of injury due to any physical, chemical, mechanical, electrical, or heat damages. In further embodiments, the subject is need of correcting baldness to restore head hair, body hair, eyelashes, eyebrows, and beard hair, and to fill in scars caused by accidents and surgery.

DETAILED DESCRIPTION OF THE INVENTION

I. Definitions

The term "Active Agent," refers to a physiologically or pharmacologically active substance that acts locally and/or systemically in the body. An active agent is a substance that is administered to an individual for the treatment (e.g., therapeutic agent), prevention (e.g., prophylactic agent), or diagnosis (e.g., diagnostic agent) of a disease or disorder. Active agents may also include materials that alleviate wrinkles, restore bulk or muscle or tissue tone, or other cosmetic used.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. A prophylactic agent refers to an agent that may prevent a disorder, disease or condition. Examples include dermal filling to prevent the onset of skin aging as a preventative measure.

The term "control" refers to an experiment performed without the active ingredient, for example without collagen composition. In other examples, controls are ones without skin grafts or hair grafts that coated with collagen composition. Controls are known in the art.

The term "tissue repair", refers to the restoration of tissue architecture and function after an injury in the context of the healing of damaged tissue. It encompasses regeneration and replacement. Regeneration refers to a type of healing in which new growth completely restores portions of damaged tissue to their normal state. Replacement refers to a type of healing in which severely damaged or non-regenerable tissues are repaired by the laying down of connective tissue, a process commonly referred to as scarring.

The term "tissue augmentation" or "soft tissue augmentation" refers to corrective procedures that are used to restore the appearance of skin, and tissue which have become less than desirable due to aging or other chemical, physical or UV damages.

The term "wound" refers to damage to a tissue or organ and can be external or internal.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The terms "enhance", "increase", "stimulate", "promote", "decrease", "inhibit" or "reduce" are used relative to a control. Controls are known in the art. For example, an increase response in a subject or cell treated with a compound is compared to a response in subject or cell that is not treated with the compound.

The term "growth factors," refers to a group of proteins or hormones that stimulate the cellular growth. Growth factors play an important role in promoting cellular differentiation and cell division, and they occur in a wide range of organisms.

The term "biocompatible" or "biologically compatible," generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein means that the materials degrades or breaks down into its component subunits, or digestion, e.g., by a biochemical process, of the material into smaller (e.g., non-polymeric) subunits.

The term "pharmaceutically acceptable," refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "molecular weight," generally refers to the relative average chain length of the bulk polymer or protein, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

II. Compositions

A. Collagen

Collagen is the principal extracellular structural protein in a mammal. At least seven types of mammalian collagen have been described. Their common characteristic is a three stranded helix, consisting of 3 polypeptide chains, called alpha-chains. All of the alpha chains have the same configuration, but differ in the composition and sequence of their amino acids, leading to different types of alpha chains However, chains all have glycine in every third position of the amino acid sequence, allowing the helical conformation to occur.

Representative collagen materials include placental collagen, recombinant human collagen, tissue engineered human-based collagen, porcine collagen, bovine collagen, autologous collagen, collagen fibers, and human tissue collagen matrix. Collagen's structural and functional properties are uniquely suited to these diverse applications. For example, collagen is useful in tissue engineering procedures in which an implanted device serves to guide proper tissue regeneration, providing structural support and a suitable surface for cell and tissue growth/regrowth. Collagen's absorbable properties minimize the likelihood of infections and other downstream adverse immunological reactions associated with the implanted material. Collagen is hemostatic, making it suitable for use in medical sponges, bandages, dressings, sutures, etc. Collagen facilitates wound healing, tissue regeneration, etc., by providing sites for cell attachment and migration. Collagen's three-dimensional structure permits effective drug and nutrient exchange with the surrounding environment and prevents build-up of waste products, etc., enabling its use in various drug delivery devices and systems, facilitating cell/tissue growth/regrowth in engineering applications, etc.

1. Sources of Collagen

Collagen or collagen-containing biomaterials can include collagen extracted from a variety of sources especially naturally derived animal tissues, preferably human tissue. In one embodiment, collagen is extracted from a human placental tissue.

In other embodiments, the collagen in the collagen composition is entirely obtained through non-natural, or synthetic sources. In further embodiments, collagen or collagen-containing tissues are a mixture of collagen derived or obtained from more than one source.

Any type of collagen may be used in the methods and compositions herein. In some embodiments, collagen type I, collagen type III, collagen type IV, collagen type VI, or a combination thereof, may be used. A collagen may be derived from cell culture, animal tissue, or recombinant means, and may be derived from human, porcine, or bovine sources. Some embodiments comprise collagen derived from human fibroblast culture. Some embodiments comprise collagen that has been denatured to gelatin. In a preferred embodiment, collagen is derived from human placentae.

Collagen concentrations vary according to the intended applications. In some embodiments, collagen may be present at a concentration of about 1 mg/mL to about 100 mg/mL, about 1 mg/mL to about 10 mg/mL, about 10 mg/mL to about 20 mg/mL, about 20 mg/mL to about 40 mg/mL, about 40 mg/mL to about 70 mg/mL, about 70 mg/mL to about 100 mg/mL, and preferably at about 35 mg/mL.

i. Human Collagen

The placenta is a complex organ that facilitates the physiological exchange between the fetus and the mother and has an extremely rich reservoir of extracellular matrix (ECM) and bioactive molecules. In the whole placenta, including the amnion, which contains collagen (types I, IV, VII, and XVII), elastin, laminin, proteoglycans, and adhesion proteins, play an important role in the maintenance of vessel walls and villous integrity (Chen C P et al., *Placenta* 24:316 (2003)). Moreover, many growth factors secreted from the mother during pregnancy, such as insulin-like growth factor-1 (IGF-1), epidermal growth factor (EGF), platelet-derived growth factor (PDGF), fibroblast growth factor-2 (FGF-2), vascular endothelial growth factor (VEGF), and transforming growth factor-$\beta$ (TGF-$\beta$), are delivered to the fetus through the placenta, suggesting that they have important roles in promoting the growth of the developing fetus (Forbes K et al., J Endocrinol. 207:1 (2010)). Furthermore, the biological properties of the placenta, such as anti-inflammatory, antibacterial, low immunogenicity, antiscarring, and wound protection, make it an ideal candidate to treat burned skin, leg ulcers, and ophthalmic disorders (Hopkinson A et al., *Tissue Eng Part C Methods.* 14:371 (2008); De D. et al., *J Cell Physiol.* 226:2033 (2011); Hong J W et al., *Ann Plast Surg.* 65:96 (2010)).

Placental tissue includes the amnion and the chorion. In certain embodiments, the collagen is extracted from pooled placental tissue. In alternative embodiments, the collagen is extracted from a single placenta. This may be particularly helpful when repeated treatments of the subject are employed. In certain embodiments, the collagen is extracted from the whole placenta. The collagen may be extracted according to disclosures in U.S. Pat. No. 5,002,071, which is incorporated by reference in its entirety herein. The collagen may be extracted by proteolytic extraction of any one or more of the following samples described in U.S. Pat. No. 5,002,071: whole placenta insoluble amnion, soluble amnion, and soluble chorion of the placenta. In certain embodiments, the placental collagen formulation is 35 mg/mL collagen in saline solution that is isotonic relative to the wound tissue.

In certain embodiments, the collagen is from a human source. In certain embodiments, the collagen is placental collagen. In certain embodiments, the collagen is extracted from whole placenta. In certain embodiments, the collagen is extracted by proteolytic digestion of a substrate selected from the group consisting of insoluble amnion, soluble amnion, soluble chorion of the placenta, and combinations thereof. In one embodiment, proteolytic digestion is with pepsin.

The human placenta can be harvested without harm to the donor and are commonly discarded. The matrix components of the placenta are similar to those of the skin and several growth factors in the placenta are involved in wound healing and angiogenesis. Therefore, the compositional and biological properties of the placenta have the potential to provide a highly favorable environment for wound healing.

In some embodiments, the human placenta is presented as a dermal substitute for the reconstitution of full-thickness wounds. Human placenta-derived extracellular matrix (ECM) sheets provide not only structural guidance for cell behaviors, but also mechanical and chemical cues for full-thickness wound healing.

In some embodiments, the collagen present in the composition is de-cellularized human placenta extracellular matrix, which contain many types of collagen including types I, IV, VII, and XVII as well as all associated growth factors and other molecules beneficial for wound healing and tissue regenerations.

In some embodiments, collagen compositions containing human sourced collagen are advantageous over compositions containing non-human sourced collagen, such as bovine collagen, when injected into humans. Injections of allogeneic compositions have a reduced immune response compared to injections of compositions containing material sourced from a different species than the recipient. Examples of an immune response include inflammation and release of chemicals including, histamine, bradykinin and serotonin, growth factors, cytotoxic factors, eicosanoids and cytokines. Eicosanoids include prostaglandins that produce fever and the dilation of blood vessels associated with inflammation and leukotrienes that attract certain leukocytes. Cytokines include interleukins that are responsible for communication between white blood cells; chemokines that promote chemotaxis, and interferons that have anti-viral effects, such as shutting down protein synthesis in a host cell.

ii. Commercial Sources

Collagen is also available from multiple commercial sources.

In some embodiments, the collagen is a commercial collagen product (e.g., ZYDERM1®, ZYDERM2®, ZYPLAST®, COSMODERM I®, or COMSMOPLAST® from Allergan; ARTEFILL® from Artes Medical; EVOLENCE® from ColBar Life Science; FG-5017 from Fibrogen; and ISOLAGEN®).

In some embodiments, the collagen composition contains a mixture of collagen extracted from animal/human tissues and collagen obtained via commercially available sources at a ratio of about 10%:90%, about 20%:80%, about 30%:70%, about 40%:60%, about 50%:50%, about 60%:40%, about 70%:30%, about 80%:20%, or about 90%:10%.

2. Types of Collagen

In some embodiments, the collagen comprises a mixture of Type I and Type III collagen. Type I collagen is the most abundant collagen of the human body and is the principal extracellular material present in scar tissue, tendons, skin, artery walls, the endomysium of myofibrils, fibrocartilage, and the organic part of bones and teeth. Type I collagen is composed of three alpha1-chains and one alpha2-chains. When clinicians speak of "collagen," they are usually referring to Type 1.

Type III collagen is present in rapidly growing tissue, particularly juvenile and healing skin. This is the collagen of granulation tissue and is produced quickly by young fibroblasts before the tougher Type I collagen is synthesized. Type III collagen has inter-chain disulfide bonds, whereas Type I collagen does not. The inter-chain disulfide bonds are one type of cross-linking and can provide additional molecular stability. An increase in cross-linked type collagen may result in a longer persistence of the collagen material when used in a subject as compared to lesser or no cross-linked materials. Cross-linked collagenous tissue, in certain embodiments, as compared to lesser or no cross-linked tissue may have one or more of the following characteristics: increased tensile or structural strength, increased resistance to enzymatic degradation, reduced antigenicity, and reduced immunogenicity.

In some embodiments, collagen having a high ratio of Type III collagen to Type I collagen may thus be particularly useful as they more closely mimic endogenous tissue. In certain embodiments, compositions containing Type III collagen is used in reducing the formation of excess scar tissue in wound healing by signaling to endogenous skin cells that there is sufficient scar tissue or young tissue already formed. In some embodiments, increasing the ratio of Type I to Type III collagen is used to enhance the durability and strength of the injected composition.

In certain embodiments, the ratio of Type III to Type I collagen is equal to or greater than 30:70, 40:60, 45:55, 50:50, 55:45, 60:40, 65:35, 70:30, 75:25, 80:20, 85:15, 90:10, or 95:5. In one embodiment, the ratio of Type III to Type I collagen is about 43:57, wherein "about" refers to ±15%.

In certain embodiments, the collagen comprises Type I and Type III collagen. In certain embodiments, the Type III collagen is at least about 30% of the weight or volume of the collagen component. In a certain embodiments, the Type III collagen is about 30%, about 40%, about 50%, about 60%, about 70%, about 80%, about 90%, about 95%, or about 100% of the weight or volume of the collagen component. In certain embodiments, Type III collagen is at least 30%, at least 40%, at least 50%, at least 60%, at least 70%, at least 80%, at least 90%, at least 95%, or at least 100% of the weight or volume of the collagen component.

In one embodiment, Type I and Type III collagen are present in a 50%:50% ratio. In preferred embodiments, the Type I and Type III collagen are present in a 50%:50% ratio, with a total collagen concentration of 35 mg/mL in saline solution that is isotonic relative to the wound tissue.

3. Modifications of Collagen

In some embodiments, the collagenous tissue is treated to increase the level of crosslinking present as compared to untreated collagen. In one embodiment, increasing the level of crosslinking is achieved by heat, gamma irradiation, or contact with a synthetic or natural crosslinking agent. A non-limiting example of a crosslinking agent is glutaraldehyde, polyethylene glycol, or formaldehyde. In certain embodiments, only Type I or Type III collagen is subjected to further crosslinking prior to use in a tissue augmentation procedure.

In another embodiment, either one or both of Type I or Type III collagen may be cross-linked. In another embodiment, Type I collagen is cross-linked and Type III collagen is cross-linked. In another embodiment, Type I is non-cross-linked and Type III collagen is noncross-linked. In another embodiment, Type I collagen is cross-linked and Type III collagen is noncross-linked. In another embodiment, Type I collagen is noncross-linked and Type III collagen is cross-linked.

The major molecular species besides collagen that are found in the extracellular matrix include the non-collagenous structural glycoproteins, elastin, and proteoglycans. The structural glycoproteins consist of fibronectin and laminin. Fibronectin is found in both the plasma and tissue forms and is capable of interacting with other components of the extracellular matrix. Another function of fibronectin is to opsonize collagen or fibrin and, by this mechanism, to regulate the cellular digestion of these substrates. Laminin is found in all basement membranes. Proteoglycans are characterized by a protein core linked to glycoaminoglycan side chains.

In some embodiments in using collagen as a biomaterial, it is important to use it in its purest and crystalline form to eliminate the non-collagenous proteins that are far more potent antigens. Once the inflammatory cycle is stimulated, the resorption of collagen occurs by the infiltrating inflammatory cells, principally macrophages and, to a lesser extent, granulocytes. These cells contain collagenase which acts to digest collagen. Skin collagen is chemotactic itself and becomes even more active by digestion with tissue collagenase into smaller peptide fragments. Chemotropism is the attraction of living protoplasm to chemical stimuli whereby the cells are attracted (positive hemotaxis) or repelled (negative chemotaxis) by acids, alkalis or other bodies exhibiting chemical properties. Various types of collagens, their alpha-chains, as well as small peptides formed by collagenase digestion have been shown to be chemotactic to dermal fibroblasts. Chemotactic migration of fibroblasts into the site of tissue injury or theoretically injected collagen can be regulated by the solubilized collagen or its degradation products. Thus, a collagen implant would not remain dormant in the tissue, but a complex series of events may occur. First, the collagen implant could be invaded by inflammatory and fibroblasts and, while being continuously resorbed, it could promote an inflammatory reaction by chemotactic properties of its degradation products. Thus, the area of collagen metabolism is not only important for collagen and other soft tissue injectable materials, but also to both normal and abnormal wound healing (i.e. hypertrophic scarring and keloids). In certain embodiments, the collagen is substantially free of noncollagenous proteins.

Analysis of the physical properties of collagen can be carried out by methods known to a person having ordinary skill in the art. A non-limiting example includes the use of differential scanning calorimetry (DSC) can be used to evaluate collagen material. Comparison of shifts in melting temperature before and after irradiation, for example, provides information on the nature of the material including phase transitions.

In some embodiments, the Type III collagen is treated with an alkaline solution such as NaOH. In some embodiments, the Type III collagen is treated with 1M NaOH lasts about one hour at about 20° C. In some embodiments, the treatment with NaOH removes any live viruses present in the collagen composition prior to the treatment. In some embodiments, the treatment with NaOH reduces disulfide bonds present in the Type III collagen. The extent of removal of the disulfide bonds can be assessed using sodium dodecyl sulfate polyacrylamide gel electrophoresis (SDS-PAGE). The chemical modification by NaOH results in the reduction or absence of dimers and/or trimers, and presence of Type III collagen alpha chain. The extent in the reduction of disulfide bonds in the Type III collagen can be varied in the final collagen compositions.

In certain embodiments, the collagen is homogenized to pass through a surgical needle. In one embodiment the surgical needle is a 25 gauge needle. In certain embodiments, the collagen is from soluble amnion of the placenta. In certain embodiments, the collagen is cross-linked and/or sterilized by gamma irradiation. In certain embodiments, the collagen layer comprises a pharmaceutical excipient.

In other embodiments, compositions contain a mixture of placental collagen with a ratio of 50% type III collagen and 50% type I collagen, at a total collagen concentration of 35 mg/mL, in saline solution that is isotonic relative to the wound tissue, and is cross-linked by exposure to 0.25 mRads of radiation. In some embodiments, there is no lidocaine present in the formulation. In other embodiments, there is lidocaine present in the formulation.

i. Atelocollagen

Insoluble collagen, if treated with a proteolytic enzyme, such as pepsin, undergoes fission at the intermolecular crosslinks and becomes soluble in dilute acids. During this treatment with pepsin, the telopeptide groups at both terminals of each collagen molecule are digested, thus leaving collagen with no telopeptide terminal ends. The collagen thus released is called atelocollagen. Since the telopeptide moiety is primarily responsible for antigenicity of collagen, atelocollagen has little antigenicity if any, which makes it very suitable for use as a medical material.

In preferred embodiments, the collagen compositions contain entirely atelocollagen. In other embodiments, the collagen compositions contain a fraction of collagen with telopeptide groups at one or both terminals of the molecule.

In a preferred embodiment, the collagen composition comprises 50% pure human Type I atelocollagen and 50% pure human Type III atelocollagen. In a further preferred embodiment, the implantation or injection of this composition of 50% pure human Type I atelocollagen and 50% pure human Type III atelocollagen results in minimal to no inflammation, whilst promoting collagen neo-synthesis, cellular proliferation and tissue colonization and regeneration.

The stable collagen compositions maintain at least one of, or all of, the following aspects after effective sterilization and/or prolonged storage: appearance, pH for use in a patient, extrusion force and/or rheological characteristics, concentration, sterility, and osmolarity.

B. Additional Therapeutic, Prophylactic or Diagnostic Agents

In some embodiments, collagen biomaterials are used in combination with one or more additional therapeutic, diagnostic, and/or prophylactic agents to facilitate healing and optionally, reduce or inhibit scarring. In some embodiments, the composition may contain one or more additional compounds to relief symptoms such as inflammation. Non-limiting examples include an antimicrobial agent, an analgesic, a local anesthetic, an anti-inflammatory agent, an immunosuppressant agent, anti-allergenic agent, an enzyme cofactor, an essential nutrient and a growth factor.

The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with particles in the formulation. In certain embodiments, one or more additional active agents may also be dissolved or suspended in the pharmaceutically acceptable carrier.

Suitable therapeutic agents include but are not limited to antibiotics, antioxidants, anti-viral agents, anti-inflammatory agents, cytokines, and growth factors such as fibroblast growth factor, hepatocyte growth factor, platelet-derived growth factor, vascular endothelial cell growth factor, and insulin-like growth factor. The amount of a second therapeutic generally depends on the tissue to be treated. Specific dosages can be readily determined by those of skill in the art. See Ansel, Howard C. et al. *Pharmaceutical Dosage Forms and Drug Delivery Systems* ($6^{th}$ ed.) Williams and Wilkins, Malvern, Pa. (1995). Alternatively, the collagen biomaterial can be used in combination with cell delivery, for example, the delivery of stem cells, pluripotent cells, somatic cells, or combinations thereof.

In other embodiments, one or more of an antimicrobial agent, an analgesic, a local anesthetic, an anti-inflammatory agent, including immunosuppressant agents and anti-allergenic agents, an enzyme cofactor, an essential nutrient and a growth factor are administered prior to, in conjunction with, subsequent to, or alternation with treatment with collagen biomaterial of the disclosure.

The additive drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704.

In some cases, the additional agent is a diagnostic agent imaging or otherwise assessing the site of application. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

1. Antimicrobial Agents

In some embodiments, collagen biomaterials are used in combination with one or more antimicrobial agents. An antimicrobial agent is a substance that kills or inhibits the growth of microbes such as bacteria, fungi, viruses, or parasites. Antimicrobial agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

Other exemplary antimicrobial agents include iodine, silver compounds, moxifloxacin, ciprofloxacin, levofloxacin, cefazolin, tigecycline, gentamycin, ceftazidime, ofloxacin, gatifloxacin, amphotericin, voriconazole, natamycin.

2. Local Anesthetics

In some embodiments, collagen biomaterials are used in combination with one or more local anesthetics. A local anesthetic is a substance that causes reversible local anesthesia and has the effect of loss of the sensation of pain. Non-limiting examples of local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and any combination thereof. In other aspects of this embodiment, the collagen composition comprises an anesthetic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. The concentration of local anesthetics in the compositions can be therapeutically effective meaning the concentration is adequate to provide a therapeutic benefit without inflicting harm to the patient.

3. Anti-Inflammatory Agents

In some embodiments, collagen biomaterials are used in combination with one or more anti-inflammatory agents. Anti-inflammatory agents reduce inflammation and include steroidal and non-steroidal drugs. Suitable steroidal active agents include glucocorticoids, progestins, mineralocorticoids, and corticosteroids. Other exemplary anti-inflammatory agents include triamcinolone acetonide, fluocinolone acetonide, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drug include ketorolac, nepafenac, and diclofenac.

In some embodiments, anti-inflammatory agents are anti-inflammatory cytokines. Exemplary cytokines are IL-10, TGF-β and IL-35. Anti-inflammatory cytokines in the context of biomaterial implant, skin grafts, and hair grafts are cytokine that induce an anti-inflammatory immune environment or suppress inflammatory immune environment. Activation of regulatory T cells, Tregs, is involved in the prevention of rejection, the induction and maintenance of peripheral tolerance of the allograft. Th17 cells are a subset of T helper cells which is characterized by the production of IL-17. Th17 cells have been suggested to play a role in allograft rejection. In some embodiments, cytokines to be added to the collagen compositions are those that induce Tregs activation (e.g. IL-25) and suppress Th17 activation (e.g. IL-10) for minimizing rejection.

4. Growth Factors

In some embodiments, collagen biomaterials are used in combination with one or more growth factors. Growth factor, also known as a cytokine, refers to a protein capable of stimulating cellular growth, proliferation, and/or cellular differentiation. Non-limiting examples of growth factors include transforming growth factor beta (TGF-β), transforming growth factor alpha (TGF-α), granulocyte-colony stimulating factor (GCSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF8), growth differentiation factor-9 (GDF9), acidic fibroblast growth factor (aFGF or FGF-1), basic fibroblast growth factor (bFGF or FGF-2), epidermal growth factor (EGF), vascular endothelial growth factor (VEGF) and hepatocyte growth factor (HGF).

5. Cofactors and Essential Nutrients

In some embodiments, the collagen composition further comprises one or more enzyme cofactors, and/or one or more essential nutrients. Exemplary cofactors include vitamin C, biotin, vitamin E, and vitamin K. Exemplary essential nutrients are amino acids, fatty acids, etc.

6. Cells and Tissues

In some embodiments, the collagen composition further comprises at least one eukaryotic cell type. Some exemplary eukaryotic cell types include stem cells, mesenchymal stem cells, keratinocytes, fibroblasts, melanocytes, adipocytes, immune cells such as T lymphocytes, B lymphocytes, natural killer cells, and dendritic cells, or combinations thereof.

In a particular embodiment, the stem cells are adipose-derived mesenchymal stem cells. Functional characteristics of mesenchymal stem cells that may benefit wound healing include their ability to migrate to the site of injury or inflammation, participate in regeneration of damaged tissues, stimulate proliferation and differentiation of resident progenitor cells, promote recovery of injured cells through growth factor secretion and matrix remodeling, and exert unique immunomodulatory and anti-inflammatory effects (Phinney D G et al., *Stem Cells,* 25:2896-2902 (2007); Chamberlain G et al., *Stem Cells,* 25:2739-2749 (2007); Dazzi F et al., *Curr Opin Oncol.* 19:650-655 (2007)).

In certain embodiments, the eukaryotic cell is responsible for increasing the structural integrity of connective tissue, promoting healing, or promoting the integration of the skin material and the wound tissue area. Furthermore, the eukaryotic cell, such as a fibroblast, is responsible for enhancing or promoting the growth or connection of cells or tissues.

In some embodiments, the collagen composition further comprises one or more biological tissues to be grafted. Exemplary biological tissues include skin materials, hair follicles, cornea and any parts of tissues or organs. The biological tissues have desired properties at the site of graft.

C. Formulations

In some embodiments, collagen compositions are packaged, for example, into sterile dosage units which can be stored and distributed for use by attending physicians. These lyophilized or fluid formulations can be in the form of sterile packaged syringes for injection, or tubes or jars of solution. The dosages for the injectables typically will be 0.25 cc/0.5 cc, 1.0 cc, 2 cc, 5 cc, 10 cc, and 20 cc. The injectables can be administered subcutaneously, supraperiosteal, or into any desired site of implant. The efficacy is determined by physician evaluations, patient self-evaluations, and Quality of life evaluations.

The sterile collagen compositions can be administered in concentrated form, diluted with sterile water or buffer, formulated as a gel, ointment or lotion, solution, or suspension. It can include additional therapeutic, prophylactic or diagnostic agent, either in the solution, gel, ointment or suspension, or as particles (nanoparticles, liposomes, microparticles) or implants.

Another embodiment provides pharmaceutical compositions and dosage forms including the described collagen composition. Pharmaceutical unit dosage forms of the compounds of this disclosure are suitable for mucosal (e.g., nasal, sublingual, vaginal, buccal, or rectal), parenteral (e.g., intramuscular, subcutaneous, intravenous, intra-arterial, or bolus injection), or topical administration to a patient. Examples of dosage forms include, but are not limited to: dispersions; ointments; cataplasms (poultices); pastes; powders; dressings; creams; plasters; solutions; patches; gels; and sterile solids suitable for parenteral administration to a patient.

The composition, shape, and type of dosage forms of the compositions of the disclosure will typically vary depending on their use. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

The formulation of the collagen composition or its injectable composition will be tailored to the individual subject, the nature of the condition to be treated in the subject, and generally, the judgment of the attending practitioner.

The pharmaceutical excipients include carriers suitable for parenteral administration. Examples of carriers are saline, buffered saline, dextrose, water, and other physiologically compatible solutions such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants).

Alternatively, formulations for parenteral use can comprise dispersions or suspensions of the components of the compositions prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, or dextran. Optionally, the suspension also can contain suitable stabilizers. Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Like the amounts and types of excipients, the amounts or de-cellularized biomaterial in a dosage form may differ depending on factors such as, but not limited to, the route by which it is to be administered to patients. Collagen concentration in an aqueous solution mixture may vary. In some embodiments, collagen may be present at a concentration of about 1 mg/mL to about 100 mg/mL, about 1 mg/mL to about 10 mg/mL, about 10 mg/mL to about 20 mg/mL, about 20 mg/mL to about 40 mg/mL, about 40 mg/mL to about 70 mg/mL, about 70 mg/mL to about 100 mg/mL, and preferably at about 35 mg/mL. However, typical dosage forms of the active collagen component of the collagen composition are in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Depending on the specific tissue to be treated, additional components may be used prior to, in conjunction with, or subsequent to treatment with collagen biomaterial of the disclosure. For example, protease inhibitors and other compounds that prevent the degradation of the collagen material can be used.

1. Solutions, Gels, Ointments and Suspensions

Numerous formulations are known and available. Solutions can be the sterile collagen composition, concentrated or diluted with water, buffered saline, or an equivalent, formed into a gel with a polysaccharide such as alginate or hyaluronic acid, polyvinyl pyrrole, or ointment such as petrolatum or mineral oil, or emulsified with lipid or oil. Emulsions are generally dispersions of oily droplets in an aqueous phase. There should be no evidence of breaking or coalescence. Suspensions contain solid particles dispersed in a liquid vehicle; they must be homogeneous when shaken gently and remain sufficiently dispersed to enable the correct dose to be removed from the container. Sediment may occur, but this should disperse readily when the container is shaken, and the size of the dispersed particles should be controlled. The active ingredient and any other suspended material must be reduced to a particle size small enough to prevent irritation and damage to the cornea. They may contain suitable additives, such as antimicrobial agents, antioxidants, and stabilizing agents.

When the solution is dispensed in a multidose container that is to be used over a period of time longer than 24 hours, a preservative must be added to ensure microbiologic safety over the period of use.

Formulations should be prepared depending on the intended use of the collagen biomaterials and are well-known to those skilled in the art. They may contain suitable additives, such as antimicrobial agents, antioxidants, and stabilizing agents.

For example, for applications in dermal filling, the pH of the formulations should be ideally equivalent to that of the targeted site such as the dermis or sub-dermis, which is about 5.5-7.3, preferably 6.5-7.0. However, the decision to add a buffering agent should also be based on stability considerations. The pH selected should be the optimum for both stability of the active pharmaceutical ingredient and physiological tolerance. If a buffer system is used, it must not cause precipitation or deterioration of the active ingredient.

Changes in pH can affect the solubility and stability of collagen and/or additional components in the formulation; consequently, it is important to minimize fluctuations in pH. The buffer system should be designed sufficient to maintain the pH throughout the expected shelf-life of the product.

The preparation of collagen and collagen compositions requires careful consideration of the need for isotonicity, a certain buffering capacity, the desired pH, the addition of antimicrobial agents and/or antioxidants, the use of viscosity-increasing agents, and the choice of appropriate packaging. Collagen compositions are considered isotonic when the tonicity is equal to that of a 0.9% solution of sodium chloride. The body tissues can usually tolerate solutions equivalent to 0.5-1.8% of sodium chloride with a pH from about 6 to about 8.

Solutions that are isotonic with the site of treatment are preferred. An amount equivalent to 0.9% NaCl is ideal for comfort and should be used when possible. The tissues can tolerate tonicities within the equivalent range of 0.6-2% NaCl without discomfort. There are times when hypertonic solutions are necessary therapeutically, or when the addition of an auxiliary agent required for reasons of stability supersedes the need for isotonicity. A hypotonic solution will require the addition of a substance (tonicity adjusting agent) to attain the proper tonicity range.

In some instances, the formulation is distributed or packaged in a liquid form. Alternatively, formulations for administration can be packed as a solid, obtained, for example by lyophilization of a suitable liquid formulation. The solid can be reconstituted with an appropriate carrier or diluent prior to administration.

Solutions, suspensions, or emulsions for administration may be buffered with an effective amount of buffer necessary to maintain a pH suitable for the intended administration. Suitable buffers are well known by those skilled in the art and some examples of useful buffers are acetate, borate, carbonate, citrate, and phosphate buffers.

Solutions, suspensions, or emulsions for administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for administration may also contain one or more preservatives to prevent bacterial contamination. Suitable preservatives are known in the art, and include polyhexamethylenebiguanidine (PHMB), benzalkonium chloride (BAK), stabilized oxychloro complexes (otherwise known as PURITE®), phenylmercuric acetate, chlorobutanol, sorbic acid, chlorhexidine, benzyl alcohol, parabens, thimerosal, and mixtures thereof.

Solutions, suspensions, or emulsions for administration may also contain one or more excipients known art, such as dispersing agents, wetting agents, and suspending agents.

In the preferred embodiments, collagen compositions do not contain any additives but are packaged in sterile form.

Formulations containing collagen compositions can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for instillation, injection or topical application. In other embodiments, the fluid can be supplied as a kit that can be stored at 4° C., at −20° C., or at −80° C. until needed. In further embodiments, the fluid can be stored lyophilized at room temperature, 4° C., at −20° C., or at −80° C. until needed.

In some embodiments, a collagen composition is substantially stable at 4° C., room temperature, at −20° C., or at −80° C. for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months.

2. Polymer Matrices

Particles can also be formed containing one or more therapeutic, prophylactic or diagnostic agents dispersed or encapsulated in a polymeric matrix. The matrix can be formed of non-biodegradable or biodegradable matrices, although biodegradable matrices are preferred. The polymer is selected based on the time required for in vivo stability, i.e. that time required for distribution to the site where delivery is desired, and the time desired for delivery.

Representative synthetic polymers are: poly(hydroxy acids) such as poly(lactic acid), poly(glycolic acid), and poly(lactic acid-co-glycolic acid), polyanhydrides, polyorthoesters, polyamides, polycarbonates, polyalkylenes such as polyethylene and polypropylene, polyalkylene glycols such as poly(ethylene glycol) (also referred to poly(ethylene oxide)), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly (methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

The in vivo stability of the matrix can be adjusted during the production by using polymers such as polylactide-co-glycolide copolymerized with polyethylene glycol (PEG). PEG if exposed on the external surface may elongate the time these materials circulate since it is hydrophilic.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

Microparticle and nanoparticles can be formed using any suitable method for the formation of polymer micro- or nanoparticles known in the art. The method employed for particle formation will depend on a variety of factors, including the characteristics of the polymers present in the polymer-drug conjugate or polymer matrix, as well as the desired particle size and size distribution. The type of therapeutic, prophylactic or diagnostic agent(s) being incorporated in the particles may also be a factor as some therapeutic, prophylactic or diagnostic agents are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

Implants can be formed from one or more polymers. In preferred embodiments, the implants are dermal implants. Suitable implants include, but are not limited to, rods, discs, and wafers.

Implants can also be formed from a polymeric matrix having one or more therapeutic, prophylactic or diagnostic agents dispersed or encapsulated therein. The matrix can be formed of any of the non-biodegradable or biodegradable polymers described above, although biodegradable polymers are preferred. The composition of the polymer matrix is selected based on the time required for in vivo stability, i.e. that time required for distribution to the site where delivery is desired, and the time desired for delivery.

The implants may be of any geometry such as fibers, sheets, films, microspheres, spheres, circular discs, rods, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling. Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Implants may be spherical or non-spherical in shape. For spherical-shaped implants, the implant may have a largest dimension (e.g., diameter) between about 5 µm and about 2 mm, or between about 10 µm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 µm and about 2 mm, or between about 10 µm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimensions are, or are similar to, implants already approved for dermal injection via needle: diameter of 460 microns and a length of 6 mm and diameter of 370 microns and length of 3.5 mm.

Implants may also be designed to be least somewhat flexible so as to facilitate both insertion of the implant, such as in the vitreous, and subsequent accommodation of the implant. The total weight of the implant is usually about 250 to 5000 µg, more preferably about 500-1000 µg. In certain embodiments, the implant has a mass of about 500 µg, 750 µg, or 1000 µg.

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more therapeutic, prophylactic or diagnostic agents present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and therapeutic, prophylactic or diagnostic agent are chosen so as to be stable at the temperatures required for manufacturing, usually at least about 85° C. However, depending on the nature of the polymeric components and the one or more therapeutic, prophylactic or diagnostic agents, extrusion methods can employ temperatures of about 25° C. to about 150° C., more preferably about 65° C. to about 130° C.

Implants may be coextruded in order to provide a coating covering all or part of the surface of the implant. Such coatings may be erodible or non-erodible, and may be impermeable, semi-permeable, or permeable to the Therapeutic, prophylactic or diagnostic agent, water, or combinations thereof. Such coatings can be used to further control release of the therapeutic, prophylactic or diagnostic agent from the implant.

Compression methods may be used to make the implants. Compression methods frequently yield implants with faster release rates than extrusion methods. Compression methods may employ pressures of about 50-150 psi, more preferably about 70-80 psi, even more preferably about 76 psi, and use temperatures of about 0° C. to about 115° C., more preferably about 25° C.

D. Kits

In some embodiments, the compositions are provided in a kit. Formulations are prepared using a pharmaceutically acceptable "carrier" composed of materials that are considered safe and effective and may be administered to an individual without causing undesirable biological side effects or unwanted interactions. These lyophilized or fluid formulations can be in the form of sterile packaged syringes for injection, or tubes or jars of solution. The dosages for the injectables will be 0.25 cc/0.5 cc, 1.0 cc, 2 cc, 5 cc, 10 cc, and 20 cc. Typically the collagen compositions will be in a single dose unit, or in a kit with a first containing with liquid to rehydrate the dry components in a second component. These may include components for administration, such as syringe and an applicator such as a needle.

III. Methods of Making

A. Manufacture of Placental Collagen

In some embodiments, collagens for use according to the methods are produced by a method including extraction from placental tissues. For example, fresh placenta is collected and the amnion is manually separated from the chorion, such as by finger separation. Both the amnion and the chorion are then cleaned of any remaining blood clots or debris. For short-term storage, the amnion and the chorion are placed in an antibiotic solution until processed. Exemplary antibiotic solutions include linomycin (3 gms/10 mL), amphotericin B (50 mg/10 mL), neomycin sulfate (0.5 gm/10 mL), polymyxin B sulfate (500,000 units/10 mL) in 1 liter of normal saline.

Collagen is extracted using limited proteolytic digestion with pepsin. In brief, tissue is homogenized in 0.5 M acetic acid, the pH adjusted to 2.5 with HCl and the preparation digested twice with pepsin (10 mg pepsin/gm wet weight tissue) overnight. A combination method of selective precipitation from neutral salt solvent and acid solvents is used to purify the collagen. Purified collagen is reconstituted by dialysis against low ionic strength sodium phosphate buffer (pH 7.2) at 15-17° C. Lidocaine was added to a final concentration of 0.3%. All procedures are carried out at 4-8° C., although other suitable temperatures can be used.

In addition, an anti-microbial agent, an anti-inflammatory agent, a growth factor, or a combination thereof, is optionally incorporated after reconstitution of the collagen, depending on the desired properties of the collagen layer.

B. Insoluble Amnion Processing

In some embodiments, collagens for use according to the methods are produced by extracting collagen from the insoluble amnion of the placenta. The amnion is stored in an antibiotic solution according to Example 1. First, the antibiotic is decanted from the amnion. Then, 5 mL of cold distilled water is added to each amnion, with subsequent homogenization of the amnion for approximately 15 minutes in polytron. The homogenized amnion is then centrifuged at 8,000×g for 15 minutes at 4° C. The supernatant is then discarded and the precipitant washed five times with acetone to remove the lipids. The precipitant is then weighed, and pepsin (Sigma, 1:10,000, from porcine stomach mucosa) 3.0 molar acetic acid per amnion was added, 15 mL or more if extra-large amnions, and the precipitant is homogenized for approximately 5 minutes in a polytron.

The mixture is allowed to stand for 18 hours at 4° C., centrifuged at 100,000×g for 1 hour at 4° C., the supernatant discarded, the precipitant weighed and then the pepsin and homogenization steps are repeated and the supernatant discarded.

In addition, an anti-microbial agent, an anti-inflammatory agent, a local analgesic, a growth factor or a combination thereof can be added to the precipitant after the supernatant is discarded and mixed, depending on the desired properties of the collagen layer.

C. Soluble Amnion Processing

An exemplary method for processing soluble amnions from the placenta comprises rinsing the antibiotics from the amnions with deionized water, adding 5 mL of cold distilled water to each amnion, homogenizing for approximately 15 minutes in a polytron and centrifuging at 8,000×g for 15 minutes at 4° C. The supernatant is discarded and lipids are removed from the precipitate by washing with acetone three times and weighing the precipitate.

Pepsin (Sigma, 1:10,000, from porcine stomach mucosa) is added to the precipitate (1:100 w/w) and 100 mL of 0.5 molar acetic acid per amnion is added, more if the amnions are extra-large, and then homogenized for approximately 10 minutes in a polytron. The pepsin is allowed to extract collagen from the precipitate for 18 hours at 4° C. and then centrifuged at 100,000×g for 1 hour at 4° C. retaining both the precipitate and the supernatant. The supernatant is again weighed, and the steps of pepsin and acetic acid addition, homogenization, pepsin extraction of collagen and centrifuging are then repeated.

The supernatants from the first and second extractions are combined and 10 molar NaOH is added drop wise to adjust the pH to from 7.0 to 7.2. The mixture is permitted to stand for 2 hours at 4° C., centrifuged at 100,000×g for 45 minutes at 4° C. and the precipitate is discarded. A 3.0M NaCl solution is added to the supernatant and permitted to stand for 2 hours at 4° C., centrifuged at 100,000×g for 45 minutes at 4° C. and the precipitate is weighed and lidocaine to 0.3% is added.

In addition, an anti-microbial agent, an anti-inflammatory agent, a growth factor or a combination thereof can be added to the precipitate and mixed, depending on the desired properties of the collagen layer.

D. Soluble Amnion Processing with Further Purification

In some embodiments, collagens extracted from soluble amnions are subject to further purification. Method of soluble amnion processing from the placenta and further purification comprises rinsing the antibiotic from the amnion with deionized water, the amnions are cut to approximately 2 cm×2 cm and washed briefly with acetone, soaked in 0.5 M acetic acid (pH adjusted to 2.5 with HCl), homogenized with a polytron for about 15 minutes, pepsin is added (1:100 pepsin/set tissue) (1 mg pepsin/1 mL solution) and stirred at 4° C. overnight, centrifuged as indicated above, retaining the supernatant. Pepsin is again added to the mixture as indicated previously and stirred at 4° C. overnight, centrifuged and the supernatant from both centrifuging steps are combined. A 2.0M NaCl solution is added to the mixture and permitted to stand overnight at 4° C. and again centrifuged, the supernatant discarded and the precipitate retained.

The precipitate is purified by dissolving it in 0.5 M acetic acid, centrifuging, and discarding the precipitate. A 2.0M NaCl solution is added to the supernatant, and permitted to stand overnight at 4° C., again centrifuged with the supernatant discarded. The resulting precipitate is dissolved in 0.5 M acetic acid, again centrifuged, and the precipitate discarded. The supernatant is dialyzed against 0.02 M $Na_2HPO_4$ thoroughly for 48 hours with frequent dialysis fluid exchanges, centrifuged, the supernatant discarded, the precipitate weighed, and solid lidocaine HCl is added to 0.30% with mechanical agitation.

In addition, an anti-microbial agent, an anti-inflammatory agent, a growth factor, or a combination thereof can be added to the precipitate and mixed, depending on the desired properties of the collagen layer.

E. Chorion Processing

In some embodiments, collagens for use according to the methods are produced by extraction from soluble chorion of the placenta. For example, in a presently preferred method of processing soluble chorion, the antibiotics are rinsed from the chorion with deionized water, the chorion is cut to approximately 2 cm×2 cm units and washed briefly with acetone and then soaked into 0.5 M acetic acid that had been adjusted to pH 2.5 with HCl. The tissue is then homogenized with a polytron to fine particles for about 15 minutes, pepsin added and centrifuged as indicated above with the supernatant being retained. The pepsin and centrifuge steps are then repeated, the supernatant of each of these steps are combined with 2M NaCl and permitted to stand overnight at 4° C. and then centrifuged again with the supernatant discarded.

For purification, the precipitate is dissolved into 0.5 M acetic acid, centrifuged, and the precipitate discarded. A 2M NaCl solution is added to the supernatant and permitted to stand overnight at 4° C., then again centrifuged and the supernatant discarded. The precipitate is dissolved into 0.5 M acetic acid, centrifuged, dialyzed against 0.02 M Na2HPO4 thoroughly for 48 hours with frequent dialysis fluid exchanges, again centrifuged, the supernatant discarded, and the precipitate weighed. Solid lidocaine HCl is added to 0.30% to the precipitate with mechanical agitation.

In addition, an anti-microbial agent, an anti-inflammatory agent, a growth factor, or a combination thereof can be added to the precipitate and mixed, depending on the desired properties of the collagen layer.

F. Cross-Linking

In other embodiments, collagen precipitates obtained by any of the foregoing preparations are treated with a radioactive source, wherein the material is sterilized and cross-linked. 15 cc of each of the foregoing resulting precipitates is placed in 20 cc serum bottles with crimp closures and placed in CE137 radioactive source for varying lengths of time in order for them to receive 0.25 M rads, 0.5 M rads, 1.0 M rads, and 2.0 M rads which serves the dual purpose of sterilizing the material and cross-linking the collagen.

G. Sterilization

In some further embodiments, collagen precipitates obtained by any of the foregoing preparations is treated with a radioactive source, wherein the material is sterilized as described in U.S. Pat. No. 7,902,145. A 0.3% to 0.5% human Type I+III collagen solution was prepared at pH 3 (lower than 5), filtered through a 0.45 m porous membrane, and then processed under a laminar flow hood in a class 1000 clean room. No bacteria were detectable in the filtered solution. The collagen is precipitated by addition of 20 mM sodium phosphate, at pH 7.2, at room temperature. The collagen paste was harvested by centrifugation in closed and sterile buckets. The 6% concentrated collagen paste was then washed and diluted to 3.5% with a sterile phosphate buffered physiological solution (PBS). Sterile 1 mL syringes were filled with the final collagen paste. After one week of storage at +4° C., each syringe was packed within its final pouch and sealed before being frozen in dry ice to about −80° C. Each layer of syringes was covered by a one inch thick layer of dry ice, within an insulated polystyrene box. The total height of the final package was less than 15 inches and it was stored at −20° C. or in dry ice until gamma-irradiation. Gamma-irradiation was performed at room temperature for less than 24 hours. The irradiation dose was >25 kGray. Some dry ice was still present in the package after irradiation and the syringes were still frozen. After thawing, the syringes were inspected. The syringes were not damaged and they were stored at room temperature for one week before being tested. The collagen paste was tested using Sodium Dodecyl Sulfate-Poly Acrylamide Gel Electrophoresis (SDS-PAGE) procedures well known to one of ordinary skill in the art.

In one embodiment, the collagen in the compositions may be treated by terminal sterilization according to disclosures in U.S. Pat. No. 7,902,145. In specific embodiments, this method further comprises freezing the collagen material and irradiating the collagen material with an effective amount of gamma or electron beam radiation to sterilize the collagen material without causing significant deterioration of the collagen material. Gamma ray or e-beam radiation is at least 5 kGy, or between 6 kGy and 8 kGy. In some embodiments, the collagen is sterilized prior to contact with the biological tissue. In other embodiments, the collagen, after sterilization, is stored and handled under sterile conditions prior to injection into a subject.

IV. Methods of Use

Methods of using collagen compositions for therapeutic, cosmetic, and prophylactic applications are provided.

In certain embodiments, compositions and/or methods of augmenting soft tissue stimulate the formation of adipocytes and/or adipocyte deposition in a subject compared to compositions and methods that do not incorporate the use of the placental collagen described herein. In certain embodiments, the compositions and/or methods of tissue augmentation promote vascularization in a subject compared to compositions and methods that do not incorporate the use of the placental collagen described herein. In more specific embodiments, the compositions and methods promote fibrovascular growth in a subject into the collagen composition, and results in a better "take" and reduced rejection of the injected composition. In certain embodiments, a non-immunogenic collagen composition and methods related to tissue augmentation are described.

Subjects that will respond favorably to the method of the invention include mammals and specifically human patients. In general, any subject who would benefit from the composition and methods of the invention relating to the collagen compositions and methods relating to tissue augmentation are appropriate for administration of the invention method. In preferred embodiments, the subject or patient is human.

The collagen or collagen composition may be retained at the site of application for an extended period of time. For example, after administration, one or more of therapeutic agent in the collagen composition remain at the site of application for at least 6 hours, at least 12 hours, at least 1 day, at least 2 days, at least 3 days, at least one week, at least 2 weeks, at least 3 weeks, at least 4 weeks, at least 5 weeks, at least 6 weeks, at least 7 weeks, at least 2 months, at least 3 months, at least 6 months, at least 9 months, at least 1 year or more.

A. Conditions to be Treated

In some embodiments, collagen compositions are useful for promoting wound healing, promote tissue regeneration, reducing scarring, promote tissue integration, or reduce tissue rejection, in particular for dermal filling, skin grafting, and hair transplantation.

1. Use of Collagen as a Dermal Filler

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

Dermal fillers are useful in treating soft tissue condition and in other skin therapies because the fillers can replace lost endogenous matrix polymers, or enhance/facilitate the function of existing matrix polymers, in order to treat these skin conditions. Collagen compositions are useful in many cosmetic applications to fill wrinkles, lines, folds, scars, and to enhance dermal tissue, such as, e.g., to plump thin lips, or fill-in sunken eyes or shallow cheeks.

In some embodiments, the collagen compositions are used to correct areas on the face like nasolabial folds, cheeks, and chin where the materials are injected in the mid and deep dermis regions. In some embodiments, the collagen compositions are used to correct superficial, fine line wrinkles, for example, tear trough, glabellar lines periorbital lines, smile lines, or forehead.

A method of treating a skin condition comprises the step of administering to an individual suffering from a skin condition a collagen composition is described, wherein the administration of the composition improves the skin condition, thereby treating the skin condition. In one embodiment, a skin condition is a method of treating skin dehydration comprises the step of administering to an individual suffering from skin dehydration a hydrogel composition, wherein the administration of the composition rehydrates the skin, thereby treating skin dehydration. In another aspect of this embodiment, a method of treating a lack of skin elasticity comprises the step of administering to an individual suffering from a lack of skin elasticity a hydrogel composition, wherein the administration of the composition increases the elasticity of the skin, thereby treating a lack of skin elasticity. In yet another aspect of this embodiment, a method of treating skin roughness comprises the step of administering to an individual suffering from skin roughness a hydrogel composition, wherein the administration of the composition decreases skin roughness, thereby treating skin roughness. In still another aspect, a method of treating a lack of skin tautness includes the step of administering to an individual suffering from a lack of skin tautness a hydrogel composition, wherein the administration of the composition makes the skin taut, thereby treating a lack of skin tautness. In a further aspect of this embodiment, a method of treating a skin stretch line or mark comprises the step of administering to an individual suffering from a skin stretch line or mark a hydrogel composition, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a hydrogel composition, wherein the administration of the composition increases skin tone or radiance, thereby treating skin paleness. In another aspect of this embodiment, a method of treating skin wrinkles comprises the step of administering to an individual suffering from skin wrinkles a hydrogel composition, wherein the administration of the composition reduces or eliminates skin wrinkles, thereby treating skin wrinkles. In yet another aspect of this embodiment, a method of treating skin wrinkles comprises the step of administering to an individual a hydrogel composition, wherein the administration of the composition makes the skin resistant to skin wrinkles, thereby treating skin wrinkles.

In some embodiments, methods of reducing appearance of fine lines in thin skin regions of a patient are provided, wherein the method generally comprises administering to the patient a dermal filler composition, at a depth of no greater than about 1 mm, collagen based dermal filler composition. In some embodiments, the composition is injected at a depth of a depth of no greater than about 0.8 mm, no greater than about 0.6 mm, or no greater than about 0.4 mm.

i. Controls

The effect of implanting collagen compositions can be compared to control. For example, in some embodiments, when the conditions to be treated are present in multiple locations on the body such as two sunken eyes or two shallow cheeks, collagen composition is injected to one of the two sunken eyes or one of the two shallow cheeks; the result from the collagen treated side is compared to the untreated but equivalent location on the same subject. In some embodiments, surgeon/practitioners can obtain controls by taking pictures of the site(s) of treatment prior to the treatment, and at defined time intervals after the treatment with collagen composition so that the effect of the treatment can be compared at the same site(s) of the same subject before and after the treatment. In some embodiments, patients will notice the significant difference within weeks, months after injection with collagen since many patients would have suffered from the skin issues for a long period of time and have clear memory of the status of their sunken eyes, facial wrinkles, and etc., prior to the treatment.

2. Use of Collagen in Skin Grafts

The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main cell types which make up the epidermis are keratinocytes, melanocytes, Langerhans cells and Merkels cells. The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

In a split thickness graft, the donor skin is mostly epidermis and only a small amount of dermis. A split thickness graft is appropriate if the wound is not deep. By comparison, in a full thickness graft, the donor skin has both epidermis and dermis. Full thickness grafts provide for better structural characteristics at the grafted site. However, a full thickness graft can add the complexity of requiring an additional graft to replace the donor skin at the donor site.

Split-thickness grafts are more fragile, especially when placed over areas with little underlying soft tissue support, and usually do not withstand subsequent radiation therapy. They can contract significantly during healing. They tend to be hypo- or hyper-pigmented, particularly in darker-skinned individuals. Their thinness, abnormal pigmentation, and frequent lack of smooth texture and hair growth make split thickness skin grafts more functional than cosmetic. When used to resurface large burns of the face, split-thickness grafts may yield an undesirable mask like appearance. Although both full-thickness and split-thickness donor sites leave a second wound, the split-thickness donor site must re-epithelialize and often causes significant discomfort and has an ongoing wound care requirement until healed. However, these sites may be re-harvested once healing is complete.

More characteristics of the normal donor skin are maintained following grafting when thick split-thickness or full-thickness skin grafts are harvested, because more collagen content, dermal vascular plexuses, and epithelial appendages are contained within thicker grafts. However, thicker grafts have higher metabolic needs. Thus, they require optimal conditions for survival and have higher incidence of graft failure than split-thickness grafts. Full-thickness grafts, on the other hand, have a better color match to the recipient site due to their thicker nature and inclusion of additional dermal structures. They tend to contract to a much lesser degree than split-thickness grafts, providing optimized cosmetic and functional results. Further, full-thickness grafts are often a better thickness match for full thickness skin/dermis defects. The donor site is typically closed primarily and requires a much less intensive wound care regimen.

In one aspect, a skin material for grafting onto a wound bed of a subject is described, and the skin material including (a) a collagen layer including collagen, and optionally a pharmaceutically acceptable excipient, wherein the collagen layer has a first and second surface; and (b) a harvested section of skin having a first and second surface, wherein the first surface comprises the outer most layer of the skin relative to the second surface; wherein the second surface of the skin contacts at least the first surface of the collagen layer.

In another aspect, a method of preparing a skin material is described herein, including (a) providing a section of harvested skin having a first and second surface, wherein the first surface comprises the outer most layer of the skin relative to the second surface; and (b) contacting a collagen layer, having a first and second surface, with at least the second surface of the harvested skin, wherein the collagen layer comprises collagen, and wherein the collagen layer optionally comprises a pharmaceutically acceptable excipient: and wherein the second surface of the skin contacts at least the first surface of the collagen layer.

In another aspect, a method of grafting skin is described, including (a) applying a collagen layer, having a first and second surface, to a wound surface of a subject, wherein the collagen layer comprises collagen; the second surface of the collagen layer is in contact with the wound surface: and the collagen layer optionally comprises a pharmaceutically acceptable excipient; and (b) applying a skin graft to at least the first collagen surface of the collagen covered wound.

In one aspect, cultivated skin material is grafted by applying the skin material over a wound area of a subject, wherein the surface of the wound area is in contact with at least the second surface of the collagen layer.

In certain embodiments, the harvested skin is autologous. In certain embodiments, the harvested skin is full-thickness or split thickness.

In certain embodiments, the collagen layer and the harvested skin both have an average thickness; and wherein the average thickness of the collagen layer is equal to or less than the average thickness of the harvested skin material.

In particular embodiments, the collagen in the skin material compositions may be treated by terminal sterilization according to disclosures in U.S. Pat. No. 7,902,145. In some embodiments, the collagen of the skin material for grafting is sterilized prior to contact with the skin material. In some embodiments, the collagen is sterilized immediately prior to contact with the wound or harvested skin. In other embodiments, after sterilization, the collagen is stored and handled under sterile conditions prior to contact with the wound.

In some embodiments, the formulation applied to a wound caused by a burn comprises two layers of collagen construct. The bottom layer contacting the wound bed is made of collagen sponge type material and seeded with dermal fibroblasts to promote dermis healing. The top layer is made of collagen membrane type material and seeded with epidermal keratinocytes to promote epidermis healing.

In certain embodiments, the collagen is a commercial collagen product (e.g. ZYDERMI, ZYDERM2, or ZYPLAST from Allergan; ARTEFILL from Artes Medical; EVOLENCE from ColBar Life Science: FG-5017 from Fibrogen: and ISOLAGEN), or a mixture of a commercial collagen product and the placental collagen described herein.

i. Wound Healing

In some embodiments, the terms "wound", "wound bed", "wound area" are used interchangeably. "Wound surface" is an area of a subject where skin normally exists but is not present. Skin is the outer covering of living tissue of an animal. In some embodiments, the subject has a wound caused by an event or condition that results in loss of skin and exposure of flesh or tissue not normally exposed. Non-limiting examples include trauma, injury, infection, disease, surgery or burn. In certain instances, the wound is any portion of the body that would benefit from the application of the skin material composition or methods of grafting skin as presented herein. Benefits include protecting the subject against pathogens, insulation, temperature regulation, synthesis of vitamin D, water resistance, protection and correction of an otherwise disfiguring or aesthetically undesirable appearance.

For example, in some embodiments, the methods are useful to treat wounds that result from a burn. A burn is a type of injury that may be caused by heat, cold, electricity, chemicals, light, radiation, or friction. Burns can be highly variable in terms of the tissue affected, the severity, and resultant complications. Muscle, bone, blood vessel, and epidermal tissue can all be damaged with subsequent pain due to profound injury to nerves. Description and classification of burns is listed in Table 1.

Most burns are first- to third-degree, with the higher-degree burns typically being used to classify burns postmortem. Below are brief descriptions of these classes. This system is however being replaced by one reflecting the need for surgical intervention. The burn depths are described as superficial, superficial partial-thickness, deep partial-thickness, or full thickness.

TABLE 1

A description of the traditional and current classifications of burns

| Nomenclature | Traditional nomenclature | Depth | Clinical findings |
| --- | --- | --- | --- |
| Superficial | First-degree | Epidermis involvement | Erythema, minor pain, lack of blisters |
| Partial thickness-superficial | Second-degree | Superficial (papillary) dermis | Blisters, clear fluid, and pain |
| Partial thickness-deep | Second-degree | Deep (reticular) dermis | Whiter appearance |
| Full thickness | Third-or Fourth-degree | Dermis and underlying tissue and possibly fascia, bone, or muscle | Hard, leather-like eschar, purple fluid, no sensation (insensate) |

First-degree burns are usually limited to redness (erythema), a white plaque and minor pain at the site of injury. These burns involve only the epidermis. Sunburns can be included as first degree burns.

Second-degree burns manifest as erythema with superficial blistering of the skin, and can involve more or less pain depending on the level of nerve involvement. Second-degree burns involve the superficial (papillary) dermis and may also involve the deep (reticular) dermis layer.

Third-degree burns occur when the epidermis is lost with damage to the subcutaneous tissue. Burn victims will exhibit charring and extreme damage of the epidermis, and sometimes hard eschar will be present. Third-degree burns result in scarring and victims will also exhibit the loss of hair shafts and keratin. These burns may require grafting.

Fourth-degree burns damage muscle, tendon, and ligament tissue, thus result in charring and catastrophic damage of the hypodermis. In some instances the hypodermis tissue may be partially or completely burned away as well as this may result in a condition called compartment syndrome, which threatens both the life and the limb of the patient. Grafting is required if the burn does not prove to be fatal.

A newer classification of "Superficial Thickness", "Partial Thickness" (which is divided into superficial and deep categories) and "Full Thickness" relates more precisely to the epidermis, dermis and subcutaneous layers of skin and is used to guide treatment and predict outcome.

An even simpler, more accurate and more descriptive classification is epidermal, dermal and full thickness. Dermal injuries are subdivided into superficial, mid and deep.

Burns can also be assessed in terms of total body surface area (TBSA), which is the percentage affected by partial thickness or full thickness burns (superficial thickness burns are not counted). The rule of nines is used as a quick and useful way to estimate the affected TBSA.

Burns are caused by a wide variety of substances and external sources such as exposure to chemicals, friction, electricity, radiation, and extreme temperatures, both hot and cold.

Most chemicals that cause severe chemical burns are strong acids or bases. Chemical burns are usually caused by caustic chemical compounds. such as sodium hydroxide, silver nitrate, and more serious compounds (such as sulfuric acid and Nitric acid). Hydrofluoric acid can cause damage down to the bone and its burns are sometimes not immediately evident.

Electrical burns are caused by an exogenous electric shock. Common causes of electrical burns include workplace injuries or being defibrillated or cardioverted without a conductive gel. Lightning is a rare cause of electrical burns. The internal injuries sustained may be disproportionate to the size of the burns seen, and the extent of the damage is not always obvious. Such injuries may lead to cardiac arrhythmias, cardiac arrest, and unexpected falls with resultant fractures.

Radiation burns are caused by protracted exposure to UV light (as from the sun), tanning booths, radiation therapy (as patients who are undergoing cancer therapy), sunlamps, and X-rays. By far the most common burn associated with radiation is sun exposure, specifically two wavelengths of light UVA, and UVB, the latter being more dangerous. Tanning booths also emit these wavelengths and may cause similar damage to the skin such as irritation, redness, swelling, and inflammation. More severe cases of sun burn result in what is known as sun poisoning.

Scalding is caused by hot liquids or gases, most commonly occurring from exposure to high temperature tap water. A blister is a "bubble" in the skin filled with serous fluid as part of the body's reaction to the heat and nerve damage. Steam is a common gas that causes scalds. The injury is usually regional and usually does not cause death. More damage can be caused if hot liquids enter an orifice. However, deaths have occurred in more unusual circumstances, such as when people have accidentally broken a steam pipe. The demographics that are of the highest risk to suffering from scalding are young children, with their delicate skin, and the elderly over 65 years of age.

A cold burn (compare frostbite) is a kind of burn which arises when the skin is in contact with a low-temperature object. They can be caused by prolonged contact with moderately cold objects (snow and cold air for instance) or brief contact with very cold objects such as dry ice, liquid helium, liquid nitrogen, liquid discharged from an upside-down gas duster, or other refrigerants. In such a case, the heat transfers from the skin and organs to the external cold object.

Subjects that will respond favorably to the method of the invention are mammals, and specifically human patients. In general, any subject who would benefit from the composition and methods of the invention relating to skin grafts are appropriate for administration of the invention method. In one embodiment, the subject or patient is human.

The wound may be treated in a method to prepare the receipt of a skin material or collagen material described herein. In certain embodiments, the wound is debrided or excised prior to contact with the collagen layer or skin material. The wound may be cleaned by washing or rinsing with a cleansing solution, such as water, saline, soap, or wound cleansing formula. The wound may be excised with a scalpel, laser or other tool to remove dead or diseased tissue. The wound may be drained, dried, or treated with heat or depressed temperatures before contact with the material.

ii. Use in Skin Material

In some embodiments, the harvested skin may be autologous. An advantage to using autologous skin is to minimize immune rejection of the graft. In certain embodiments, the donor tissue from the autologous skin graft may come from skin located on a body part well-removed from the wound site and not generally exposed to ultraviolet radiation. In alternative embodiments, the harvested skin is allogeneic or xenogeneic. Allograft, cadaver skin or homograft is ordered from the local skin bank. Xenograft, or animal skin, is ordered from a medical supply company. Autograft is surgically removed from the patient using a dermatome or other skin removing device such as a scalpel or blade.

In certain embodiments, the harvested skin graft has been meshed prior to contact with the collagen. This technique allows expansion of the graft surface area up to about 9 times the donor site surface area. This technique is indicated when insufficient donor skin is available for large wounds, as in major burns or when the recipient site is irregularly contoured and adherence is a concern. The graft is placed on a carrier and passed through a meshing device using methods well known to a person having ordinary skill in the art.

The harvested skin is a full-thickness or split-thickness graft. If the entire thickness of the dermis is included, it is termed full-thickness graft. In some embodiments, the harvested skin is a full-thickness graft. In this instance, both dermal and epidermal layers of skin form the donor tissue used for the skin graft. A secondary split-thickness skin graft may be needed to help the donor tissue wound to heal.

If less than the entire thickness of the dermis is included, this graft is referred to as a split-thickness skin graft. These grafts are categorized further as thin (from about 0.005 to about 0.012 in, or from about 0.1 mm to about 0.3 mm), intermediate (from about 0.012 to about 0.018 in, or from about 0.3 mm to about 0.45 mm), or thick (from about 0.018 to about 0.030 in, or from about 0.45 to about 0.75 mm), based on the thickness of the harvested graft. Based on reconstructive needs, split-thickness skin grafts meeting the above criteria can be readily harvested using commercial dermatomes. In certain embodiments, the harvested skin is a split thickness graft. Primarily epidermis forms the donor tissue used, with a slight amount of dermal tissue also used. The split-thickness skin graft is advantageous if the wound heals more easily and avoids the need for a secondary split-thickness skin graft on top of the secondary wound created in harvesting the donor tissue. In certain embodiments, the harvested skin is about 0.1 mm to about 1.0 mm thick. In other embodiments the harvested skin is about 0.40 mm thick. In certain embodiments, harvested skin is a full- or split-thickness graft.

In certain embodiments the harvested skin has a first and second surface, wherein the first surface is the epidermal layer or is closer to the epidermal layer relative to the second surface. The terms 'first surface' and 'second surface' with respect to harvested skin are intended to distinguish two sides of a harvested skin graft. The first surface of the harvested skin is typically the surface exposed to the environment and is referred to as the 'outer' layer. The second surface of the harvested skin is typically in contact with the collagen layer and/or wound surface and is generally not exposed to the environment and is referred to the 'inner' layer. The second surface of the harvested skin is the dermal layer or is closer to the dermal layer relative to the first surface. The second surface can even be the epidermal layer in very thin harvested grafts, but is still the surface closer to the dermal layer of the donor site relative to the first surface. The exact compositions of the harvested skin are in part dependent on the thickness of the harvested graft and the depth of harvesting.

In some embodiments, the average collagen layer thickness and the average harvested skin thickness are roughly equal, with less than about a 20% difference in thickness between the two layers. In some embodiments, the average thickness of the collagen layer is less than the average thickness of the harvested skin layer. In a certain embodiments, the difference between the average thickness of the two layers is less than about 100%, about 90%, about 80%, about 70%, about 60%, about 50%, about 40%, about 30%, about 20%, or about 10%. Thickness may be calculated from dimension through the layer as opposed to its length or width. In certain embodiments, the layer of harvested skin, skin material, and/or collagen layer has roughly a uniform thickness. A roughly uniform thickness refers to less than about 20% in thickness variance of a single layer.

In certain embodiments, the skin material compositions and/or methods of skin grafting stimulate the formation of adipocytes and/or adipocyte deposition in a subject compared to skin material compositions and methods that do not incorporate the use of the placental collagen described herein. In certain embodiments, the skin material compositions and/or methods of skin grafting stimulate vascularization in a subject compared to compositions and methods that do not incorporate the use of the placental collagen described herein. In more specific embodiments, the compositions and methods promote fibrovascular growth in a subject into the grafted skin material, and results in a better "take" of the graft and reduced rejection of the skin material. In certain embodiments, the invention provides a non-immunogenic biocompatible skin composition and methods related to skin grafts.

iii. Applying Skin Material to the Wound

An exemplary method includes the following steps:

In the first step, the length, width, and depth of the wound are measured to determine the size of the donor site. In some embodiments, the skin is meshed and the graft will cover an equal or larger area than the wound. In some embodiments, if the wound is going to be excised rather than debrided, the depth of the lesion may increase dramatically and a larger piece of skin will be required for coverage. In other embodiments, the template for the dermatome is smaller, equal, or larger than the area of treatment.

In the second step, the measurements are drawn at the donor site for guidance. In some embodiments, this is done with a surgical marking pen. In some embodiments, the donor sites are any one or more locations of the outer thigh, the inguinal ligament region, the posterior leg, the lateral malleolus, the popliteal fossa, or the dorsal foot. The area is prepped for example, with sterile mineral oil. In some embodiments, the template and dermatome blade also are coated with a thin layer of the oil. In a particular embodiment, the thickness of the graft is from about 0.0008 of an inch to about 0.020 of an inch. The thickness is determined at the time of surgery.

In the third step, at the donor site, the tongue blades are placed distal and proximal for the purpose of applying some tension. In one example, the dermatome is positioned at approximately a 45-degree angle so the underlining skin markings can be visualized before taking the skin. One skilled in the art would know an appropriate amount of donor skin has been procured. In some embodiments, the donor site is then allowed to sanguinate for several minutes before it is covered with xeroform (Medline Industries, Inc. Mundelein. Ill.) gauze.

In the fourth step, the donor skin is transferred to a skin graft carrier in preparation for meshing. In some embodiments, atraumatic forceps is used to prevent tearing the skin. The clinician should make certain that the dermal carrier is ridged side up or the skin will not mesh.

In some embodiments, the skin is prepped with saline, gently spread out so no curled edges or air bubbles are visible, and the carrier is placed in the mesher. In some embodiments, the skin is covered with moistened saline gauze until ready for application to the recipient site. In an alternative embodiment, the gauze is removed and a very thin layer of the collagen layer is applied to the dermal layer of the graft.

In the fifth step, the wound site is debrided with cold steel or excised. For example, the edges of the wound will need to be "freshened" or excised and then flushed with jet lavage to thoroughly cleanse the wound bed. In some embodiments, all bleeders are clamped and/or cauterized at this time to prevent the formation of hematoma. In some embodiments, a thin collagen layer is applied to the surface of the wound bed at this point. In other embodiments, the application of a collagen layer to the surface of the wound bed is omitted.

In the sixth step, the carrier is held adjacent to the wound, and the skin is teased off this device and placed directly over the defect. In some embodiments, the harvested skin had been placed on the carrier dermal side up, so repositioning is unnecessary. In some embodiments, the collagen layer is sandwiched between the dermal surface of the skin graft and the surface of the wound bed. In some embodiments, the graft is then stapled in place. Sutures, steri-strips, or non-adherent dressings also can be used for this purpose.

In the seventh step, the stent dressing is fabricated for example, by creating sutures opposing each other at the wound site. In some embodiments, the materials used to fabricate this dressing is a moistened gauze in a large piece of Vaseline® gauze (Chesebrough-Ponds Inc., Greenwich, Conn.) is folded, creating a "ball" of petroleum jelly. In some embodiments, this gauze is applied to the wound site and sutured in place with long sutures.

In the eighth step, the donor site is dressed for example, with xeroform, sterile gauze, and a mild compression dressing. In some embodiments, paper tape is also acceptable.

In the ninth step, the wound is dressed for example, with sterile gauze, fluffs, ABD pads or combine dressing (SUR-GIPAD, Johnson and Johnson, Arlington, Tex.), and a soft gauze wrap. In some embodiments, a posterior splint is applied under a double 6-inch Ace (Becton, Dickinson, and Company, Franklin Lakes, N.J.) wrap.

In the last step, the patient is discharged for example after a period of stay in hospital, with no weight bearing on the affected limb. In some embodiments, the original dressing is left intact for approximately 1 week unless deleterious signs such as pain, fever, or bleeding are present.

iv. Controls

The effect of implanting skin graft with the addition of collagen compositions can be compared to control. For example, in some embodiments, collagen composition is applied to 50%, 60%, 70%, 80%, or 90% of the site of graft so the effect can be compared to the portion that was absent of any added collagen composition. In some embodiments, many other attempts at healing the wound might have failed; practitioners can obtain controls by taking pictures of the site(s) of treatment prior to the treatment, and at defined time intervals after the treatment with collagen composition so that the effect of the treatment can be compared at the same site(s) of the same subject. In some embodiments, patients will notice the significant improvement at the site of skin graft within weeks, months after injection with collagen.

3. Use of Collagen in Hair Transplantation

In one aspect, the method of the invention is intended to increase the rate of survival of implanted hair grafts in a subject that has undergone a hair transplantation procedure.

In one aspect, the invention provides a method of improving the survival of one or more hair grafts in a subject including the steps of (a) providing a hair graft that comprises at least one hair follicle; (b) implanting the hair graft into a recipient section of skin of a subject; and (c) contacting at least a portion of the hair graft and/or the recipient site with composition including collagen.

In one embodiment, the implanting step comprises forming an opening in the surface of recipient section of skin capable of accommodating at least the hair graft; placing the collagen composition into the opening; and placing the hair graft into the opening such that contact with the collagen composition is made.

In one embodiment, initial contact between the collagen composition and the graft occurs during the implantation step, wherein the implanting step comprises forming an opening in the surface of recipient section of skin capable of accommodating at least the hair graft; placing the collagen-containing composition into the opening; and placing the hair graft into the opening such that contact with the collagen-containing composition is made.

In another embodiment, initial contact between the collagen composition and the hair graft occurs prior to implantation of the graft and the graft remains in contact with the composition during the implanting step. The collagen composition may, if desired, be contacted with the hair graft after the graft is harvested and prepared for implantation.

In one embodiment, the method comprises contacting the recipient site and at least a portion of the hair graft with a composition including collagen.

In one aspect, the invention provides a method to optimize the conditions of a recipient site of a hair graft including contacting the recipient site and at least a portion of the hair graft with a composition including collagen.

In one embodiment, an injectable composition including the collagen composition is injected below the surface of the donor skin prior to harvesting the hair graft. The injectable composition may be injected in the epidermis layer, dermis layer, subcutaneous layer, or any combination thereof. Injection of the composition into the donor site helps reduces the transaction of hair follicles during harvesting, and helps improve healing after graft harvesting. In one embodiment, the presence of the collagen composition in contact with the donor site helps reduce the appearance of scars after graft harvesting.

In another aspect, the invention provides a method to optimize the conditions of a recipient site of a hair graft including contacting the tissues of the recipient site and at least a portion of the hair graft with a collagen-containing composition. The injectable composition may be injected in the recipient site epidermis layer, dermis layer, subcutaneous layer, or any combination thereof. The presence of the collagen composition in the contact with the tissues of the recipient site improves healing after graft implantation, and helps increase the rate of hair graft survival as compared to hair grafts implanted into areas that are not in contact with the collagen composition.

In one embodiment, an injectable composition including the collagen composition is injected below the surface of the recipient skin prior to implanting the hair graft.

In one embodiment, at least the lower one-third of the surface of the hair follicle is contacted with the collagen composition, or at least the lower one-half of the surface of the hair follicle is contacted with the collagen composition In one embodiment, the hair graft is autologous.

In one embodiment, the hair graft is harvested from a donor site, which is the temporal or the occipital region of scalp.

In one embodiment, the recipient section of skin is scalp, facial region, chest, arm pit or pubic region.

In certain embodiments, the collagen is from a human source. In certain embodiments, the collagen is placental collagen. In certain embodiments, the collagen is extracted from whole placenta. In one embodiment, the collagen comprises Type III and Type I collagen, wherein the ratio of Type III collagen to Type I collagen is equal to or greater than about 30:70 (Type III:Type I). In alternative embodiments, the collagen comprises Type III and Type I collagen, wherein the ratio of Type III collagen to Type I collagen is equal to or greater than about 40:60; 43:57; 45:55; 50:50; 55:45; 60:40; 65:35; 70:30; 75:25; 80:20; 85:15; 90:10 or 95:5.

The collagen-containing composition may further comprise a pharmaceutically acceptable excipient, or further comprises at least one additional component selected from the group consisting of an anti-microbial agent, a growth factor, an analgesic, a local anesthetic, at least one type of eukaryotic cell, and any combination thereof. In one embodiment, the cell type is selected from the group consisting of keratinocytes, stem cells, melanocytes, adipocytes, and Tcells.

In one embodiment, the collagen is cross-linked and/or sterilized by gamma irradiation.

In one embodiment, the collagen is homogenized to pass through a 30 gauge surgical needle.

In one embodiment, the donor section of skin comprises any section of skin including hair follicles.

In one embodiment, the prepared hair graft is dipped into a collagen-containing composition prior to implantation.

In one embodiment, the forming the opening in the recipient site and placing the collagen-containing composition into the opening are completed in one step.

In certain embodiments, subjects that benefit from the methods of the invention have a malady or condition affecting hair growth. In certain embodiments, the subjects have a malady or condition selected from the group consisting of Alopecia prematura, Alopecia areata, Alopecia cicatrisata, woolly hair nevus, androgenetic alopecia, telogen effluvium, trichotillomania, tinea capitis, cicatricial alopecia, traction alopecia, and syphilis.

Telogen effluvium is characterized by excessive and early entry of hairs into the telogen phase. Causes of telogen effluvium and subsequent hair loss include physiologic effluvium of the newborn, postpartum effluvium, early stages of androgenetic alopecia, injury or stress, high or prolonged fever (e.g., malaria), severe infection, severe chronic illness, severe psychologic stress (life-threatening situations), major surgery, hypothyroidism and other endocrinopathies, severe dieting or malnutrition, drugs and toxins, antikeratinizing agents (e.g., etretinate [Tegison]), anticoagulants (especially heparin), antithyroid agents, alkylating agents, anticonvulsants, or hormones.

Recipient sites for hair grafts include scalp, the facial region, armpit or chest region or the pubic region. Specific areas of the facial region include eyebrows, eyelid, mustache, sideburn, chin and cheeks. More importantly, the recipient site is any area of skin wherein the appearance of hair is desired by the subject.

In one embodiment, the donor hair graft produces hair having characteristics that are desirable in the recipient section of skin. Characteristics include color, shape, texture, and length.

In one embodiment the hair graft comprises 1-5 hair follicles.

'Standard graft' as used herein refers to a round, 4-mm diameter graft.

'Minigraft' as used herein encompasses a large variety of species and is any graft that contains more than one follicular unit but is smaller than a 4-mm standard graft. More specifically, the minigraft contains three to eight hair follicles. Minigrafts may be variously placed into recipient sites that are created as round holes, slits or slots. These sites are made with steel instruments, such as punches, blades, needles, etc., as well as lasers which vaporize the tissue at the recipient site.

'Micrografts' contain one to two hair follicles.

'Follicular unit' grafts as used herein usually comprise a small group of hairs and follicles in a configuration that naturally exists on the scalp. Most patients average about 2 hairs per follicular unit. In some embodiments, a follicular unit comprises a single hair. In some embodiments, the follicular unit grafts are trimmed in a 'skinny' fashion, and possess minimal tissue left around the follicular structures. In some embodiments, the follicular unit grafts are trimmed in a fashion wherein more tissue is left surrounding the graft and is known as 'chubby'. Grafts which are trimmed in an intermediate fashion or moderately close represents the way most hair surgeons prepare them. In certain embodiments, 'hair grafts' are synonymous with a follicular unit.

The various types of grafts, as used herein, comprise the hair and follicle, and optionally the surrounding tissue that accompanies a harvested graft, such as subcutaneous and dermal tissue. In some embodiments, grafts comprise fat, pluripotent stem cells, keratinocyte, sebaceous gland epidermis, fibroconjunctive tissue, melanocytes or any combination thereof. Grafts have various shapes including, linear, rectangular, round, chubby and skinny.

In certain embodiments, the hair graft comprises at least one hair follicle. One or more associated structures of a hair follicle are selected from the group consisting of papilla, bulb of hair, medulla of hair, cortex of hair, outer root sheath, inner root sheath, dermic coat, connective tissue, hair matrix, a collection of epithelial cells interspersed with pigment producing cells, melanocytes, root sheath, hair fiber, arrector pili muscles, sebaceous glands, apocrine sweat glands. Depending on the harvesting of the hair graft, any combination of these structures accompanies a hair follicle.

In certain embodiments, the method provides for a collagen-containing composition to be in contact with 1) an implanted hair graft and 2) the recipient tissue into which the hair graft is implanted.

In certain embodiments, the contact between the collagen composition and the implanted hair and the collagen composition and the surrounding tissues of the recipient site promotes nutritional perfusion from surrounding tissues into the graft and increases the survival rate of the graft compared to a graft implanted without the use of the collagen composition. In certain embodiments, the contact between the collagen composition and the implanted hair, and between the collagen composition and the surrounding tissues of the recipient site promotes vascularization around the implanted grafts, such that the survival rate of the graft is increased compared to a graft implanted without the use of the collagen composition.

In one aspect, the hair graft is contacted with collagen. In one embodiment, a follicular unit is contacted with collagen. In one embodiment, a follicle is in contact with collagen. In one embodiment, at least one-half of the upper follicle or lower follicle is in contact with collagen.

Donor hair can be obtained from areas containing hairs with characteristics desired at the recipient site. For example, hair in the temporal area of the scalp is finer than hair in the occipital area of the scalp. Temporal hair is used for the hairline, eyebrows, and eye-lashes because of its finer nature. The difference in dermal thickness and consequently the length of the follicular unit below the skin may explain this difference. The dermis is approximately 3-5 mm thick in the temporal area and 4-5 mm thick in the occipital area. This means the thickness of the dermis is on average 1 mm less in the temporal area than in the occipital area.

Harvesting of the donor region can be done by various methods including follicular unit extraction, wherein one follicular unit at a time is removed from the donor area. In some instances, this method is carried out with a sharp, hollow, cylindrical trephine which can be driven mechanically or by a motor system.

Another technique includes the strip harvesting technique wherein a strip containing multiple follicular units from the donor are is removed and then divided into grafts (or follicular units). With the aid of a special scalpel holder and three to four blades, several strips of skin can also be removed. Another technique is to use No. 10 blades on a surgical handle with 0.8-1.0 cm spacers between the blades. These are then divided into mini or micro grafts. The donor site, which can be as wide as 20 mm and up to 12 cm long, is then closed directly with sutures. In other embodiments, the donor site is less than 15 mm wide. In one embodiment, the donor site is less than 10 mm wide.

The donor site is 'pumped up' to facilitate harvesting by injecting a large volume of saline solution together with an anesthetic. The saline helps with hemostasis and through increased turgor reduces the transection of hair follicles. In some embodiments, a solution containing collagen and anesthetic is used in the injected volume. The presence of the collagen component may aid in the healing of the donor site and reduce the appearance of scars.

Because the donor strip area is long and thin, the resulting donor wound is not wide, thus allowing for closure with very little tension of the sutures.

The harvested strips are then divided into small pieces, or 'slivered' as it is known. Slivering may involve grasping the small slivers by the fatty tissue beneath the skin, dissecting out the fat down to 1-2 mm below the hair follicle. The prepared grafts are kept in a petri dish on gauze swabs soaked in chilled saline solution or on saline soaked tongue blades that sit in a saline solution.

The subcutaneous layer thickness in both these areas is the same, about 2-3 mm. In both areas, the terminal hair transverses the dermis and is embedded approximately 1 mm into the subcutaneous tissue. This makes the temporal hair follicular depth, on average, 1 mm less than occipital hair.

Non-limiting examples of hair implanters include the Knu implanter, Choi implanter, Rapid Fire Hair Implanter Carousel (Carousel), and the hair implanter pen. There are many types of implanters and many methods of implanting hair depending on the area to be treated, the preference of the practitioner, among many other factors. A skilled practitioner should be able to determine the device and method for implanting for each particular case. More importantly, in some embodiments, the device and methods should permit the hair graft to make contact with the collagen composition at some point in the process.

Likewise, there are different methods of harvesting hair grafts from a subject. A skilled practitioner should be able to determine method for harvesting hair grafts.

Method of hair transplantation are known in the art (Hair Transplantation Unger, W. P., Shapiro, R. 4th edition. 2004 New York: M. Dekker; Hair Transplantation, the Art of Micrografting and Minigrafting, Barrera, A., Baker, A. Baker, D. L. 2002, Quality Medical Pub. St. Louis, Mo.; and Hair Transplantation 2006, Elsevier, Haber, R. S., Stough, D. B).

i. Controls

The effect of implanting hair graft with the addition of collagen compositions can be compared to control. For example, in some embodiments, collagen composition is applied to 50%, 60%, 70%, 80%, or 90% of all the hair graft so the effect can be compared to the portion of hair follicles that were grafted without any added collagen composition. Likewise, when collagen composition is applied to the donor sites of hair follicles for wound healing, controls are the donor sites without any collagen composition added. In some embodiments, practitioners can obtain controls by taking pictures of the site(s) of hair transplantation prior to the treatment, and at defined time intervals after the treatment with added collagen composition so that the effect of the treatment can be compared at the same site(s) of the same subject.

B. Dosages and Dosing Regimens

Dosage and dosing regimens are dependent on the intended use of the formulation, and is known to those skilled in the art.

In the case of sustained or controlled release formulations, gels, implants or injections into the desired site, the dosages will be modified to deliver a therapeutically equivalent amount.

The formulation of the collagen layer will be tailored to the individual subject, the nature of the condition to be treated in the subject, and generally, the judgment of the attending practitioner. In yet another embodiment, the formulation is collagen in a concentration of 35 mg/mL in a saline solution that is isotonic relative to the wound tissue.

C. Kits

In some embodiments, the compositions are provided in a kit. Formulations are prepared using a pharmaceutically acceptable "carrier" composed of materials that are considered safe and effective and may be administered to an individual without causing undesirable biological side effects or unwanted interactions. Typically the collagen composition will be in a single dose unit, or in a kit with a first containing with liquid to rehydrate the dry components in a second component. These may include components for administration, such as a syringe with a needle.

The present invention will be further understood by reference to the following non-limiting examples.

EXAMPLES

Example 1: Manufacture of a Skin Material

Collagen is extracted according to the preparations described. However, collagen obtained by methods described above or any other methods know to one skilled on the art is used. The composition of the collagen includes 0.3% lidocaine and has a ratio of 70% Type III collagen to 30% Type I collagen.

The collagen layer is then sterilized immediately before being joined to the skin layer. In this procedure, the collagen layer is frozen at a temperature of −20° C. Then, the collagen layer is treated with 8 kGy of radiation, resulting in a sterility assurance level of $10^6$ SAL for the collagen layer. The collagen is thawed to room temperature and a thin layer of the collagen is applied to the dermal side of a harvested skin section. The harvested skin is autologous and is a split-thickness graft that has been shaped to approximate the shape of the wound.

Alternatively, the placental collagen used in the manufacture of the skin material contains about 50% type III collagen and about 50% type I collagen, at a total collagen concentration of 35 mg/mL, in saline solution that is isotonic relative to the wound tissue, and is cross-linked by exposure to 0.25 mRads of radiation. There is no lidocaine present in this formulation. The resulting skin material is sterile and is ready for transplantation or can be prepared for storage.

Example 2: Skin Material with Growth Factor

The skin material is prepared according to Example I. However, before terminal sterilization, EGF is added to the collagen layer. The EGF is effective to further increase the rate of healing of the wound than occurs using the skin graft of Example 1.

Example 3: Applying the Skin Material to the Wound

The skin material, as prepared in Example 1, consists of the collagen layer and the harvested skin layer. The skin material is placed on the surface of a cleaned wound. The appropriate dressing is provided such that the wound heals and is protected from the environment or physical disturbances. The graft is periodically checked to ensure proper healing, adherence to the recipient tissue and drainage. The skin layer adheres well to the recipient tissue and is as strong and supple as the surrounding skin, due to the presence of the collagen.

In an alternative procedure, the collagen layer and harvested skin is applied in two separate steps to the wound. A thin layer of sterile collagen as prepared according to Example 1 is applied across the surface of a debrided wound. An autologous, split-thickness graft shaped in the form of the wound is applied dermal side to the surface of the wound.

Example 4: Applying the Skin Material to the Wound

In an alternative procedure, the skin graft containing collagen is placed on the surface of a cleaned wound, where the wound is due to a burn. Prior to the collagen layer being joined to the harvested skin layer, the harvested skin layer may, if needed, be meshed prior to contact with the collagen. This technique allows expansion of the graft surface area up to about 9 times the donor site surface area. This technique is indicated when insufficient donor skin is available for large wounds, as in major burns or when the recipient site is irregularly contoured and adherence is a concern. The graft is placed on a carrier and passed through a meshing device using methods known in the art.

Example 5: Applying the Skin Material to the Wound

This example details the application of the skin material including a collagen layer and a harvested skin graft to a wound. In this case, the skin is meshed prior to application of the collagen layer. This example further describes processes wherein the collagen layer is either applied first to the dermal surface of the skin graft prior to placement on the wound bed. or wherein the collagen layer is applied directly on the surface of the wound bed, followed by placement of the skin graft, dermal surface to the collagen-covered wound bed.

Step 1. The length, width, and depth of the wound are measured to determine the size of the donor site. All undermining must be taken into account and excised before grafting. When the skin is meshed, it will cover a larger surface area. If the wound is going to be excised rather than debrided, the depth of the lesion may increase dramatically and a larger piece of skin will be required for coverage. The template for the dermatome also should be selected at this time.

Step 2. The measurements are carefully drawn at the donor site with a surgical marking pen. The donor site can be in various locations, including the outer thigh, the inguinal ligament region, the posterior leg, the lateral malleolus, the popliteal fossa, or the dorsal foot. The area is then prepped with sterile mineral oil. Tongue blades work best in the application of this substance as gauze will absorb too much of the oil. The template and dermatome blade also are coated with a thin layer of the oil. At this juncture, the thickness of the graft is determined and can range from 0.0008 of an inch to 0.020 of an inch. Each patient has different requirements (the thinner the graft, the better the "take").

Step 3. At the donor site, the tongue blades are placed distal and proximal for the purpose of applying some tension. The dermatome is positioned at approximately a 45-degree angle so the underlining skin markings can be visualized before taking the skin. The dermatome moves downward until contact is made with the skin. The instrument then moves almost parallel to the donor site. Steady and equal pressure is applied while the skin is under tension until the appropriate amount of donor skin has been procured. The dermatome is then slowly angulated upward, releasing the skin from the site. During this process, having an assistant tease the skin from the dermatome to prevent it from getting caught in the blade is important. The donor site is then allowed to sanguinate for several minutes before it is covered with XEROFORM (Medline Industries, Inc. Mundelein. Ill.) gauze.

Step 4. The donor skin is transferred (dermal side up to avoid any confusion regarding orientation) to a skin graft carrier in preparation for meshing (the skin will curl toward the dermis). Atraumatic forceps should be used to prevent tearing the skin. The clinician should make certain that the dermal carrier is ridged side up or the skin will not mesh. This side of the carrier is usually marked; clinicians can feel the ridges with their fingers.

The skin is prepped with saline, gently spread out so no curled edges or air bubbles are visible, and the carrier is placed in the mesher. As the skin is being meshed, an assistant should tease the skin away from the mesher to prevent shredding. The skin is covered with moistened saline gauze until ready for application to the recipient site. In an alternative method, B, the gauze is removed and a very thin layer of the collagen layer is applied to the dermal layer of the graft.

Step 5. The wound site should be debrided with cold steel or excised. During debridement, the edges of the wound will need to be "freshened" or excised and then flushed with jet lavage to thoroughly cleanse the wound bed. All bleeders are clamped and/or cauterized at this time to prevent the formation of hematomas. A thin collagen layer is applied to the surface of the wound bed at this point. In alternative method B. the application of a collagen layer to the surface of the wound bed is omitted.

Step 6. The carrier is held adjacent to the wound, and the skin is teased off this device and placed directly over the defect. The harvested skin had been placed on the carrier dermal side up, so repositioning is unnecessary. The collagen layer is now sandwiched between the dermal surface of the skin graft and the surface of the wound bed. The graft is then stapled in place. Sutures, steri-strips, or non-adherent dressings also can be used for this purpose.

Step 7. A stent dressing is fabricated by creating at least four long sutures opposing each other at the wound site. Several materials can be used to fabricate this dressing. For example, a moistened gauze in a large piece of Vaseline® gauze (Chesebrough-Ponds Inc., Greenwich, Conn.) is folded, creating a "ball" of petroleum jelly. This gauze is applied to the wound site and sutured in place with long sutures. This dressing creates continuous compression of the harvested skin against the wound bed.

Step 8. The donor site is dressed with XEROFORM, sterile gauze, and a mild compression dressing. Paper tape is also acceptable.

Step 9. The wound is dressed with sterile gauze, fluffs, ABD pads or combination dressing (SURGIPAD, Johnson and Johnson, Arlington, Tex.), and a soft gauze wrap. A posterior splint is applied under a double 6-inch Ace (Becton, Dickinson, and Company, Franklin Lakes, N.J.) wrap.

Step 10. The original dressing is left intact for approximately 1 week unless deleterious signs such as pain, fever, or bleeding are present.

The gauze at the donor site is usually removed several days postoperatively; the xeroform gauze is usually left intact and allowed to dry to peel off. Although this appears to be contrary to the precepts of moist wound healing, it seems to be the most efficient and least problematic option for the patient.

Use of a placental-derived collagen layer can enhance the results of skin transplantation.

Example 6: General Technique in Hair Transplantation

The procedure is performed with the patient under local anesthesia: 2% lidocaine with 1:100,000 epinephrine and diazepam for mild sedation. The lateral aspect of the occipital region is used as the selected donor site because this area contains the greatest number of single-hair follicular units as well as hairs with the finest diameter. The collagen-containing composition is injected beneath the surface of the donor area. A donor strip is excised from the occipital scalp after clipping hair in the donor area to a length of 1 cm to 1.5 cm. The donor area is closed with sutures, which are generally removed 10 days postoperatively. The healing of the donor site is hastened and evidence of scarring is reduced.

The next step is to produce single-hair follicular unit grafts from the harvested donor tissue. After the excised strip is placed on a block of birch wood, it is divided into smaller segments using a No. 20 scalpel blade carefully positioned between the hair follicles. With the same blade, each segment is cut into follicular units, which are then split into single-hair grafts. The cut is made between the follicular units and at the same angle as the hair follicles grow. The grafts are trimmed to eliminate all unneeded dermis and subcutaneous tissue resulting in clean and neatly trimmed grafts that fit into the 21-gauge needle of the Choi implanter. Grafts that are clean and closely trimmed allow for implantation with a greater density than grafts that have the surrounding dermis attached. This method of creating single-hair follicular unit grafts is different from the use of "slivering" or a microscope, which, however, can be used if the patient does not have a combination of high hair-shaft caliber and low follicular unit density, traits which are common in the typical Asian patient. In Caucasian patients, microscopic dissection of follicular units is commonly employed. These methods and techniques of follicular dissection are known to a person having ordinary skill in the art.

The prepared follicular units are dipped into a collagen-containing composition prior to implantation.

A mechanical hair transplantation device, such as the "Choi" implanter may be used to simultaneously make the incision and plant the graft. Hair grafts are inserted into the needle of the Choi implanter by means of jeweler's forceps. In the instance wherein the hair graft was dipped into the collagen composition, at least a portion of the hair graft maintains contact with the collagen composition as the graft is loaded into the implanting device. The needle is then inserted into the skin at the desired angle and the plunger pushed. The needle automatically withdraws, leaving the hair follicle neatly tucked under the skin and the ring around the needle holds the single-hair graft in place while the needle is withdrawn. Once the graft is in place gentle pressure is applied with a swab while the adjacent hair grafts are inserted. The grafts require neither dressings nor bandages. Alternatively, the collagen-containing composition is injected into the area beneath the surface of the recipient area of the subject, prior to insertion of the hair graft.

Throughout the cutting and grafting process, all grafts and donor tissue are maintained in sterile petri dishes holding chilled saline solution and the dishes are supported on frozen packs.

Example 7: Measurement of Hair Graft Survival Rate

This example provides methods in how to compare the survival rate of follicular units implanted by methods with follicular units that were not contacted with a collagen-containing composition, and to evaluate the fate of grafted hair according to time.

Two templates of 1.5 cm2 are made by tattooing on both sides of the frontoparietal recess areas in 11 patients with male pattern baldness. One-hair unit micrografts are implanted in the left template using methods and one-hair unit micrografts in the right template, which were prepared in the absence of the collagen composition. Then, the surviving number of follicular units is counted at 1 and 3 months and total hairs at 6 and 12 months after transplantation.

The mean survival rate by the number of follicular units is calculated at 1 and 3 months after transplantation, respectively. The mean survival rate by the total number of hairs is also calculated at 6 and 12 months after transplantation, respectively.

Example 8: Collagen Composition for Dermal Filling

The purpose of this study was to evaluate the local tissue effects and the cellular colonization of three collagen materials following intradermal injection in humans. Three types of collagen materials were used including type I and III human collagen precipitate, Type I human collagen precipitate, and Type I and III human collagen composition, known as HUMALLAGEN®.

Materials and Methods
Human Subject

The human subject under study is a 71-year old Caucasian male. Three types of collagen materials were used for intradermal injection into the human subject, and these include type I and III human collagen precipitate (reference A or A3), type I human collagen precipitate (reference B or B3), and HUMALLAGEN® (reference C or C3). HUMALLAGEN® is a human collagen composition containing 50% pure Type I collagen and pure 50% Type III collagen. The sites of implant for collagen compositions A, B, and C were right arm/down, left arm/up, and left arm/down, respectively. Visual inspection and biopsy samples were collected 44 days and 89 days after the injection of collagen compositions.

Forty-four days after injection, one biopsy per article was collected from the subject. Paraffin histopathology, including qualitative and semi-quantitative analyses of the local tissue effects and cellular colonization was conducted. Eighty-nine days after injection, one biopsy per article was collected from the subject. Paraffin and resin histopathology, including qualitative and semi-quantitative analyses of the local tissue effects and cellular colonization was conducted.

Histologic Preparation

The three biopsies were dehydrated in alcohol solutions of increasing concentration, cleared in xylene and embedded in paraffin blocks. Three serial transversal sections were prepared using a microtome (MICROMO, France): one section was stained with modified Masson's Trichrome (MT) for general morphology and extracellular matrix evaluation; one section was stained with Safranin-Hematoxylin-Eosin (SHE) for analysis of the inflammatory reaction; one section was stained with Movat Pentachrom (MP) to identify the article.

Histopathologic Analysis

The sections were evaluated using a Nikon Eclipse 80i microscope fitted with ×2, ×10, ×20 and ×40 objectives coupled with a digital camera Nikon.

TABLE 2

Definition of ISO 10993-6 grading for histopathologic analysis. The index used is defined as 0: absent 1: slight, 2: moderate, 3: marked, 4: severe.

| Cell type/Response | Score | | | | |
|---|---|---|---|---|---|
| | 0 | 1 | 2 | 3 | 4 |
| Polymorphonuclear cells | 0 | Rare. 1-5/phf | 6-10/phf | Heavy infiltrate | Packed |
| Lymphocytes | 0 | Rare. 1-5/phf | 6-10/phf | Heavy infiltrate | Packed |
| Plasma cells | 0 | Rare. 1-5/phf | 6-10/phf | Heavy infiltrate | Packed |
| Macrophages | 0 | Rare. 1-5/phr | 6-10/phf | Heavy infiltrate | Packed |
| Giant cells | 0 | Rare. 1-2/phf | 3-5/phf | Heavy infiltrate | Sheets |
| Fibrin | 0 | Slight | Moderate | Marked | Severe |

TABLE 2-continued

Definition of ISO 10993-6 grading for histopathologic analysis. The index used is defined as 0: absent 1: slight, 2: moderate, 3: marked, 4: severe.

| Cell type/Response | Score | | | | |
|---|---|---|---|---|---|
| | 0 | 1 | 2 | 3 | 4 |
| Necrosis | 0 | Slight | Moderate | Marked | Severe |
| Fibrosis | 0 | Slight | Moderate | Marked | Severe |
| Fibroblasts | 0 | Slight | Moderate | Marked | Severe |
| Adipocytes | 0 | Slight | Moderate | Marked | Severe |
| Neovessels | 0 | Minimal capillary proliferation focal. 1-3 buds | Groups of 4-7 capillaries with supporting fibroblastic structures | Broad bank of capillaries with supporting structures | Extensive band of capillaries with supporting fibroblastic structures |
| Tissue integration | 0 | Slight | Moderate | Marked | Complete |
| Tissue ingrowth | 0 | Slight | Moderate | Marked | Complete |
| Material degradation | 0 | Slight | Moderate | Marked | Severe (100% degraded) |
| Material debris | 0 | Slight | Maderate | Marked | Severe | phf = per high powered (400×) field

Results
Day 44 Post Injection

A total of 6 paraffin sections were analyzed for the day 44 samples. The semi-quantitative histopathologic results are presented in Table 3.

TABLE 3

Semi-quantitative histopathologic analysis at 44 days post injection.

| Time Period | Patient | Article | Site | Polymorphonuclear cells | Lymphocytes | Plasma cells | Macrophages | Giant cells/Osteoclasts | Fibrin | Necrosis | Fibrosis |
|---|---|---|---|---|---|---|---|---|---|---|---|
| 44 Days | JLT | A | right arm/down | 0 | 1 | 0 | 1 | 0 | 0 | 0 | 0 |
| | | B | left arm/up | / | / | / | / | / | / | / | / |
| | | C | left arm/down | 0 | 2 | 0 | 2 | 0 | 1 | 1 | 0 |

| Time Period | Patient | Article | Site | Fibroblasts | Adipocytes | Neovessels | Tissue integration | Tissue ingrowth | Material degradation | Material debris |
|---|---|---|---|---|---|---|---|---|---|---|
| 44 Days | JLT | A | right arm/down | 1 | 0 | 1 | 4 | 1 | 1 | 3 |
| | | B | left arm/up | / | / | / | / | / | / | / |
| | | C | left arm/down | 2 | 0 | 2 | 4 | 2 | 2 | 3 |

The histopathologic analysis of samples collected at forty-four days after injection showed the presence of the test article material in two of three biopsies submitted for analysis. Test article B could not be recovered (sampling issue), The test article A was well integrated into the surrounding dermal and hypodermal tissues with no local adverse effects and test article C, well integrated as well, induced more local inflammation (moderate grade).

Biopsy A: The test article was intradermal and hypodermal. Photomicrographs of biopsy sections were taken at the site of injection 44 days after the injection of collagen composition A including a section stained with Safranin-Hematoxylin-Eosin at 20× magnification, a section stained with modified Masson's Trichrome (MT) at 2× magnification; and a section stained with Movat Pentachrom (MP) at 10× magnification. The article appeared as material granules well integrated within the dermis and the hypodermal fat cells. Signs of test article dislodgment were attributed to the sampling and technical preparation. No evidence of fibrosis or fibroplasia was observed. Fibroblasts and macrophages infiltrated the test article (slight grade) with slight signs of material phagocytosis. No significant tissue changes were observed around the test article.

Biopsy B: No test article was found on the sections prepared. The sampling might have been performed laterally relative to the actual material site.

Biopsy C: The test article was intradermal and hypodermal. Photomicrographs of biopsy sections were taken at the site of injection 44 days after the injection of collagen C including a section stained with Safranin-Hematoxylin-Eosin (SHE) at 20× magnification, a section stained with modified Masson's Trichrome (MT) at 10× magnification, a second section stained with MT at 10× magnification, and a section stained with Movat Pentachrom (MP) at 4× magnification. The article appeared as material granules well integrated within the dermis and hypodermal fat cells. Signs of test article dislodgment were attributed to the sampling and technical preparation. No evidence of fibrosis was observed. Macrophages, lymphocytes and fibroblasts infiltrated the test article (moderate grade) with moderate signs of material phagocytosis and fibroplasia. Slight signs of necrosis were suspected in limited areas. Neovessels of moderate grade were formed within the newly formed tissue surrounding and growing within the article. No other tissue changes were observed around the test article.

Day 89 Post Injection

A total of 9 paraffin sections were analyzed. The semi-quantitative histopathologic results are presented in Table 4.

The histopathologic analysis of samples collected at eighty-nine days after injection showed the presence of the test article in all three biopsies submitted for analysis. The test article A3 was well integrated into the surrounding dermal and hypodermal tissues with no local adverse effects. A small amount of the test article B3 was retrieved. It appeared well integrated into the surrounding dermal and hypodermal tissues with no local adverse effects even though a moderate lymphocytic reaction could be peripherally observed. The test article C3, well integrated as well, induced more local inflammation (marked grade).

nificant tissue changes were observed around the test article. This material showed noticeable signs of good local tolerance.

Biopsy B3: The test article was intradermal and hypodermal. Photomicrographs of biopsy sections were taken at the site of injection 89 days after the injection of collagen composition B including a section stained with Safranin-Hematoxylin-Eosin (SHE) at 10× magnification; a section stained with modified Masson's Trichrome (MT) at 4× magnification; a section stained with Movat Pentachrom (MP) at 10× magnification; a section stained with MP at 2× magnification; and a second section stained with MP at 10× magnification. The article appeared as material granules well integrated within the dermis and the hypodermal fat cells. A limited amount of test article material was found. No evidence of fibrosis was observed. Discreet signs of fibroplasia were noted. Fibroblasts, PMNs and macrophages infiltrated the test article (slight grade) with slight signs of material phagocytosis. A moderate grade of lymphocytes infiltrated the surrounding of the test article in a limited area.

Biopsy C3: The test article was intradermal and hypodermal. Photomicrographs of biopsy sections were taken at the site of injection 89 days after the injection of collagen composition C including a section stained with Movat Pentachrom (MP) at 2× magnification; a section stained with Safranin-Hematoxylin-Eosin (SHE) at 10× magnification, a

TABLE 4

Semi-quantitative histopathologic analysis at 44 days post injection.

| Time Period | Patient | Article | Site | Polymorphonuclear cells | Lymphocytes | Plasma cells | Macrophages | Giant cells/ Osteoclasts | Fibrin | Necrosis | Fibrosis |
|---|---|---|---|---|---|---|---|---|---|---|---|
| 89 Days | JLT | A3 | right arm/down | 0 | 0 | 0 | 1 | 0 | 0 | 0 | 0 |
|  |  | B3 | left arm/up | 1 | 2 | 0 | 1 | 0 | 0 | 0 | 0 |
|  |  | C3 | left arm/down | 1 | 3 | 1 | 2 | 0 | 1 | 0 | 0 |

| Time Period | Patient | Article | Site | Fibroblasts | Adipocytes | Neovessels | Tissue integration | Tissue ingrowth | Material degradation | Material debris |
|---|---|---|---|---|---|---|---|---|---|---|
| 89 Days | JLT | A3 | right arm/down | 1 | 0 | 2 | 4 | 3 | 1 | 3 |
|  |  | B3 | left arm/up | 1 | 1 | 1 | 4 | 3 | • | 1 |
|  |  | C3 | left arm/down | 2 | 2 | 2 | 4 | 4 | 1 | 3 |

Biopsy A3: The test article was intradermal and hypodermal. Photomicrographs of biopsy sections were taken at the site of injection 89 days after the injection of collagen composition A including a section stained with Safranin-Hematoxylin-Eosin (SHE) at 2× magnification; a section stained with SHE at 20× magnification; a section stained with modified Masson's Trichrome (MT) at 2× magnification; a section stained with Movat Pentachrom (MP) at 10× magnification; and a second section stained with Movat Pentachrom (MP) at 4× magnification. The article appeared as material granules well integrated within the dermis and the hypodermal fat cells. No evidence of fibrosis was observed. Discreet signs of fibroplasia were noted. Fibroblasts and macrophages infiltrated the test article (slight grade) with slight signs of material phagocytosis. No sigsecond section stained with SHE at 10× magnification, a section stained with modified Masson's Trichrome (MT) at 10× magnification. The article appeared as material granules well integrated within the dermis and hypodermal fat cells. No evidence of fibrosis was observed. Noteworthy, a marked grade of lymphocytes infiltrated the test article. Plasma cells and PMNs of slight grade infiltrated the test article. Fibroblasts and macrophages of moderate grade infiltrated the granules with signs material phagocytosis. A moderate grade of fibroplasia was noted.

Five months after the initial injection, the subject reported that he could still feel some remnants in the skin where collagen compositions A and C were injected. This was a demonstration of its very slow degradation, when injected into the dermis, up to the fat, not subcutaneously.

The presence of mature adipocytes which have apparently migrated from the hypodermis side towards the upper side of the dermis is not due to the implant, whether type I or type I+III collagen, but more likely in relation to sebaceous glands and/or hair follicles which are on the top and around for all significant areas. These adipocytes should not be interpreted as "migrating adipocytes". Based on this understanding, the numbers of adipocytes present within the implanted sited shown in the histological sections were very low.

The inflammatory reaction towards C3 (type I+III collagen made by the HUMALLAGEN® process) may be explained by the low osmolality of the gel. It is the result of significant cell necrosis and swelling around the implant which has induced the local diffusion of fibrin and migration of inflammatory cells, including macrophages, polymorphonuclear cells and lymphocytes to clean the area. On the contrary the type I+III collagen precipitate of A3 (same composition as C3, but different process) is perfectly iso-osmotic. The tolerance was exceptionally good.

Overall, the compositions containing both I and/or type III collagens showed superior safety, stability and biocompatibility. A further augmentation effect can be achieved by subsequent injections at the site on as-needed basis. Human placental collagen implantation will further enhance the healing and tissue repairing at the site by providing a stimulating environment for stems cells within specific human tissues such as in cell therapy.

Example 9: Collagen Composition for Dermal Filling

Material and Method

The human subject under study was a 40-year old healthy Asian male. Incisional wounds about 5-6 cm length were made on his bilateral post-auricular regions through the epidermis and dermis. After the incision, 0.6 ml of HUMALLAGEN® was injected to the left incision but right-side post-auricular region received no HUMALLAGEN®. The bilateral post-auricular regions were sutured with nylon thread and were removed 7 days later. As the control group, nothing was injected to the right post-auricular region. 8 weeks after the surgical procedure, scarring samples were taken at the site of incision. The degrees of scarring were assessed histologically and macroscopically. For macroscopic analysis, photographs were taken directly by iSCOPE 50× Skin and Hair Density Exam Camera.

Results

The appearances on each wound were recorded for 8 weeks after the incision. Upon visual examination, the left-side post-auricular region where HUMALLAGEN® was injected had an impression of having less scars after two months. Furthermore, the control side gave an impression of having hard tissue hyperplasia due to the scar, which made it difficult to extract tissue from. Scarring samples were extracted at the sites of incision at 8 weeks. The degrees of scarring were further assessed histologically and macroscopically. Macroscopic images taken by iSCOPE 50× showed that the right-side post-auricular region, or the control side had a wider suture wounds compared to the left-side post-auricular region. Histological images taken at 4× magnification and with 20× magnification indicated that both left and right post-auricular regions contained scar tissue, although more dermal fibrosis was observed in the control side. Four months after the suture with or without HUMALLAGEN®, the appearances on each wound were further recorded. The left-side post-auricular region where HUMALLAGEN® was injected remained with an impression of having less scars compared to the right-side post-auricular region although no further histology was carried out at this time point.

Although in experiments using rats had an acknowledge hyperplasia of fat cells growing under the dermis 8 weeks after the collagen injection (Seifert A W et al., Nature 489(7411): 561-565 (2012)), such pathological findings were not observed in humans. Increased productions of collagen fiber were not observed in humans either.

I claim:

1. A composition for tissue repair or wound healing comprising:
   Type I human atelocollagen and Type III human atelocollagen in an amount effective to promote wound healing at a site of surgery, injury, or wound relative to an untreated control;
   wherein the total collagen present in the composition comprises about 50% Type I human atelocollagen and about 50% Type III human atelocollagen;
   wherein the Type I human atelocollagen and the Type III human atelocollagen are derived from a source of collagen comprising insoluble amnion from human placenta, soluble amnion from human placenta, and soluble chorion from human placenta, or a combination thereof;
   wherein the Type I human atelocollagen and Type III human atelocollagen are extracted through proteolytic digestion by treating the source of collagen with pepsin, such that the source of collagen undergoes fission at one or more intermolecular crosslinks and becomes soluble in dilute acids; and
   wherein the proteolytic digestion digests one or more telopeptide groups on the source of collagen, thereby leaving the Type I human atelocollagen and the Type III human atelocollagen with no telopeptide terminal ends.

2. The composition of claim 1, wherein the Type I human atelocollagen and the Type III human atelocollagen is derived from collagen extracted from the human placental tissue without the use of an alkaline solution.

3. The composition of claim 1, wherein the composition further comprises Collagen Type IV, Collagen Type VII, Collagen Type XVII, elastin, laminin, a proteoglycan, an adhesion protein, or a combination thereof.

4. The composition of claim 1, wherein the Type I human atelocollagen and the Type III human atelocollagen are sterilized by exposure to 8 kGy of radiation, resulting in a sterility assurance level of $10^6$ SAL.

5. The composition of claim 1, wherein the composition is exposed to 0.25 mRads of radiation to manufacture a skin material.

6. The composition of claim 1, further comprising one or more compounds selected from the group consisting of antibacterial compounds, antifungal compounds, anti-inflammatory agents, growth factors, or a combination thereof.

7. The composition of claim 1, further comprising one or more cells selected from the group consisting of stem cells, epidermal stem cells, dermal stem cells, placenta stem cells, and cord blood stem cells, hair follicle cells, or a combination thereof.

8. The composition of claim 1, further comprising a pharmaceutically acceptable excipient for injection.

9. The composition of claim 1, wherein the composition is diluted with saline or buffer.

10. The composition of claim 1, wherein the composition is formulated into a gel, paste, solution or suspension.

11. The composition of claim 1, wherein the composition is formulated as a hydrogel.

12. A method for promoting wound healing, promoting tissue regeneration, reducing scarring, reducing local inflammation, or improving cosmetic appearance comprising:
   administering to a subject in need thereof an effective amount of the composition of claim 1.

13. The method of claim 12, wherein the composition is injected at a site of surgery, injury, or wound.

14. The method of claim 12, wherein the composition is topically applied at a site of surgery, injury, or wound.

15. The method of claim 12, wherein the composition is administered to the subject to fill wrinkles, lines, folds, scars, or to enhance dermal tissue.

16. The method of claim 12, wherein the composition is administered to the subject to restore head hair, body hair, eyelashes, eyebrows, or beard hair, or to fill in scars.

17. The method of claim 12, wherein the composition is administered to the subject at a site of injury, wherein the injury is due to physical, chemical, mechanical, electrical, heat, sunlight, or radiation damage.

18. The method of claim 12, further comprising repeating the administration of the composition of claim 1.

* * * * *